United States Patent
Lee et al.

(10) Patent No.: US 12,310,673 B2
(45) Date of Patent: *May 27, 2025

(54) FLOATING ELECTROMAGNETIC FIELD GENERATOR SYSTEM AND METHOD OF CONTROLLING THE SAME

(71) Applicant: Auris Health, Inc., Santa Clara, CA (US)

(72) Inventors: Jason Lee, Milpitas, CA (US); Christopher Sramek, Half Moon Bay, CA (US); Gregory J. Kintz, Santa Cruz, CA (US); David S. Mintz, Mountain View, CA (US); Alan Yu, Union City, CA (US)

(73) Assignee: Auris Health, Inc., Santa Clara, CA (US)

( * ) Notice: Subject to any disclaimer, the term of this patent is extended or adjusted under 35 U.S.C. 154(b) by 360 days.

This patent is subject to a terminal disclaimer.

(21) Appl. No.: 17/738,703

(22) Filed: May 6, 2022

(65) Prior Publication Data

US 2022/0331015 A1    Oct. 20, 2022

Related U.S. Application Data

(63) Continuation of application No. 15/438,589, filed on Feb. 21, 2017, now Pat. No. 11,324,554.
(Continued)

(51) Int. Cl.
*A61B 34/20*    (2016.01)
*A61G 13/08*    (2006.01)
*A61G 13/12*    (2006.01)

(52) U.S. Cl.
CPC ............ *A61B 34/20* (2016.02); *A61G 13/08* (2013.01); *A61G 13/1235* (2013.01); *A61B 2034/2051* (2016.02)

(58) Field of Classification Search
CPC ............ A61B 34/20; A61B 2034/2051; A61B 2090/376; A61G 13/08; A61G 13/1235; A61G 13/107
See application file for complete search history.

(56) References Cited

U.S. PATENT DOCUMENTS 1,011,038 A  *  12/1911  Davenport ........... A61G 13/009
                                                          606/245
3,428,307 A  *   2/1969  Kennedy ............... A61B 6/04
                                                          108/138
(Continued)

OTHER PUBLICATIONS

Advisory Action for U.S. Appl. No. 15/438,589, dated Dec. 4, 2020, 3 pages.
(Continued)

*Primary Examiner* — Myles A Throop
(74) *Attorney, Agent, or Firm* — Paradice & Li LLP

(57) ABSTRACT

Floating electromagnetic field generator systems and methods are provided. The system comprises a surgical bed portion. The system also comprises a brace component disposed within the surgical bed portion. Additionally, the system comprises a first arm that is attached to the brace component. The first arm is positioned adjacent to the surgical bed portion. Additionally, the first arm has at least one field generator coil embedded therein. The system also comprises a second arm that is attached to the brace component. The second arm is positioned adjacent to the surgical bed portion. Additionally, the second arm has at least one field generator coil embedded therein. The second arm is positioned parallel to the first arm.

20 Claims, 32 Drawing Sheets

Related U.S. Application Data

(60) Provisional application No. 62/320,193, filed on Apr. 8, 2016.

(56) References Cited

U.S. PATENT DOCUMENTS

| | | | |
|---|---|---|---|
| 3,620,210 A * | 11/1971 | Annas | A61H 1/02 601/24 |
| 3,751,028 A * | 8/1973 | Scheininger | A61B 6/04 5/601 |
| 4,173,228 A | 11/1979 | Steenwyk et al. | |
| 5,253,647 A | 10/1993 | Takahashi et al. | |
| 5,318,025 A | 6/1994 | Dumoulin et al. | |
| 5,429,132 A | 7/1995 | Guy et al. | |
| 5,558,091 A | 9/1996 | Acker et al. | |
| 5,592,939 A * | 1/1997 | Martinelli | A61B 5/062 128/899 |
| 5,727,553 A | 3/1998 | Saad | |
| 5,913,168 A | 6/1999 | Moreau et al. | |
| 6,004,271 A | 12/1999 | Moore | |
| 6,253,770 B1 | 7/2001 | Acker et al. | |
| 6,310,573 B1 | 10/2001 | Samuelsson | |
| 6,530,913 B1 | 3/2003 | Giba et al. | |
| 6,544,230 B1 | 4/2003 | Flaherty et al. | |
| 6,572,535 B2 | 6/2003 | Watanabe et al. | |
| 6,593,884 B1 | 7/2003 | Gilboa et al. | |
| 6,610,007 B2 | 8/2003 | Belson et al. | |
| 6,636,757 B1 | 10/2003 | Jascob et al. | |
| 6,669,709 B1 | 12/2003 | Cohn et al. | |
| 6,690,963 B2 | 2/2004 | Ben-Haim et al. | |
| 6,904,630 B2 | 6/2005 | Al-Kassim et al. | |
| 6,905,460 B2 | 6/2005 | Wang et al. | |
| 6,944,492 B1 * | 9/2005 | Persoons | A61B 5/055 5/601 |
| 7,371,210 B2 | 5/2008 | Brock et al. | |
| 7,789,874 B2 | 9/2010 | Yu et al. | |
| 8,146,874 B2 | 4/2012 | Yu | |
| 8,302,221 B1 * | 11/2012 | Camp, Jr. | A61G 5/125 5/81.1 RP |
| 8,505,137 B1 * | 8/2013 | Gaines, Jr. | A61B 6/0487 5/601 |
| 8,706,193 B2 | 4/2014 | Govari et al. | |
| 8,932,207 B2 | 1/2015 | Greenburg et al. | |
| 8,968,333 B2 | 3/2015 | Yu et al. | |
| 9,226,687 B2 | 1/2016 | Soper et al. | |
| 9,301,726 B2 * | 4/2016 | Mackie | A61B 6/032 |
| 9,314,306 B2 | 4/2016 | Yu | |
| 9,326,822 B2 | 5/2016 | Lewis et al. | |
| 9,408,669 B2 | 8/2016 | Kokish et al. | |
| 9,452,018 B2 | 9/2016 | Yu | |
| 9,504,604 B2 | 11/2016 | Alvarez | |
| 9,561,083 B2 | 2/2017 | Yu et al. | |
| 9,566,201 B2 | 2/2017 | Yu | |
| 9,622,827 B2 | 4/2017 | Yu et al. | |
| 9,636,184 B2 | 5/2017 | Lee et al. | |
| 9,713,509 B2 | 7/2017 | Schuh et al. | |
| 9,727,963 B2 | 8/2017 | Mintz et al. | |
| 9,737,371 B2 | 8/2017 | Romo et al. | |
| 9,737,373 B2 | 8/2017 | Schuh | |
| 9,744,335 B2 | 8/2017 | Jiang | |
| 9,763,741 B2 | 9/2017 | Alvarez et al. | |
| 9,788,910 B2 | 10/2017 | Schuh | |
| 9,818,681 B2 | 11/2017 | Machida | |
| 9,844,412 B2 | 12/2017 | Bogusky et al. | |
| 9,867,635 B2 | 1/2018 | Alvarez et al. | |
| 9,918,681 B2 | 3/2018 | Wallace et al. | |
| 9,931,025 B1 | 4/2018 | Graetzel et al. | |
| 9,949,749 B2 | 4/2018 | Noonan et al. | |
| 9,955,986 B2 | 5/2018 | Shah | |
| 9,962,228 B2 | 5/2018 | Schuh et al. | |
| 9,974,501 B2 | 5/2018 | Hartmann et al. | |
| 10,016,900 B1 | 7/2018 | Meyer et al. | |
| 10,022,192 B1 | 7/2018 | Ummalaneni | |
| 10,136,959 B2 | 11/2018 | Mintz et al. | |
| 10,145,747 B1 | 12/2018 | Lin et al. | |
| 10,159,532 B1 | 12/2018 | Ummalaneni | |
| 10,231,793 B2 | 3/2019 | Romo | |
| 10,231,867 B2 | 3/2019 | Alvarez et al. | |
| 10,244,926 B2 | 4/2019 | Noonan et al. | |
| 10,285,574 B2 | 5/2019 | Landey et al. | |
| 10,299,870 B2 | 5/2019 | Connolly et al. | |
| 10,482,599 B2 | 11/2019 | Mintz et al. | |
| 10,517,692 B2 | 12/2019 | Eyre et al. | |
| 10,524,866 B2 | 1/2020 | Srinivasan et al. | |
| 10,617,374 B2 | 4/2020 | Hartmann et al. | |
| 10,639,114 B2 | 5/2020 | Schuh et al. | |
| 10,646,279 B2 | 5/2020 | Maraghoosh et al. | |
| 10,667,875 B2 | 6/2020 | DeFonzo et al. | |
| 10,677,910 B2 | 6/2020 | Reniers | |
| 10,702,346 B2 | 7/2020 | Popovic et al. | |
| 10,722,140 B2 | 7/2020 | Izmirli et al. | |
| 10,820,954 B2 | 11/2020 | Marsot et al. | |
| 2001/0009976 A1 | 7/2001 | Panescu et al. | |
| 2001/0029366 A1 | 10/2001 | Swanson et al. | |
| 2001/0047133 A1 | 11/2001 | Gilboa et al. | |
| 2002/0065455 A1 | 5/2002 | Ben-Haim et al. | |
| 2002/0087169 A1 | 7/2002 | Brock et al. | |
| 2002/0095730 A1 * | 7/2002 | Al-Kassim | A61B 6/0442 5/601 |
| 2002/0167313 A1 | 11/2002 | Taimisto | |
| 2002/0177789 A1 | 11/2002 | Ferry et al. | |
| 2003/0052785 A1 | 3/2003 | Gisselberg et al. | |
| 2003/0074011 A1 | 4/2003 | Gilboa et al. | |
| 2003/0129750 A1 | 7/2003 | Schwartz | |
| 2003/0135204 A1 | 7/2003 | Lee et al. | |
| 2004/0162480 A1 * | 8/2004 | Satragno | A61B 5/055 5/601 |
| 2004/0162487 A1 | 8/2004 | Klingenbeck-Regn et al. | |
| 2004/0172757 A1 * | 9/2004 | Somasundaram | A61G 13/02 5/601 |
| 2004/0176751 A1 | 9/2004 | Weitzner et al. | |
| 2004/0193146 A1 | 9/2004 | Lee et al. | |
| 2004/0199072 A1 * | 10/2004 | Sprouse | A61B 5/062 5/601 |
| 2004/0220461 A1 | 11/2004 | Schwartz | |
| 2005/0143944 A1 | 6/2005 | Cech et al. | |
| 2005/0182295 A1 | 8/2005 | Soper et al. | |
| 2005/0197767 A1 | 9/2005 | Nortrup | |
| 2006/0116571 A1 | 6/2006 | Maschke et al. | |
| 2006/0185091 A1 | 8/2006 | Jackson | |
| 2006/0241397 A1 | 10/2006 | Govari et al. | |
| 2007/0016007 A1 | 1/2007 | Govari et al. | |
| 2007/0025527 A1 * | 2/2007 | Eichenseer | A61B 6/032 5/601 |
| 2007/0049797 A1 | 3/2007 | Yoshida et al. | |
| 2007/0060879 A1 | 3/2007 | Weitzner et al. | |
| 2007/0208252 A1 | 9/2007 | Makower | |
| 2007/0244388 A1 | 10/2007 | Sato et al. | |
| 2008/0195109 A1 | 8/2008 | Hunter et al. | |
| 2008/0245946 A1 | 10/2008 | Yu | |
| 2008/0300592 A1 | 12/2008 | Weitzner et al. | |
| 2009/0054884 A1 | 2/2009 | Farley et al. | |
| 2009/0064413 A1 * | 3/2009 | Sliski | A61B 5/415 5/601 |
| 2009/0126113 A1 | 5/2009 | Hejkal et al. | |
| 2009/0139030 A1 * | 6/2009 | Yang | A61G 13/10 5/619 |
| 2010/0016757 A1 | 1/2010 | Greenburg et al. | |
| 2010/0319121 A1 * | 12/2010 | Polomsky | A61G 7/1076 5/81.1 RP |
| 2010/0324412 A1 | 12/2010 | Govari et al. | |
| 2011/0066029 A1 | 3/2011 | Lyu et al. | |
| 2012/0053453 A1 | 3/2012 | Graumann | |
| 2012/0158011 A1 | 6/2012 | Sandhu et al. | |
| 2012/0172712 A1 | 7/2012 | Bar-tal | |
| 2012/0174317 A1 * | 7/2012 | Saracen | A61B 6/0487 901/29 |
| 2012/0241576 A1 | 9/2012 | Yu | |
| 2013/0158346 A1 | 6/2013 | Soper et al. | |
| 2013/0162775 A1 | 6/2013 | Baumann et al. | |
| 2014/0033432 A1 * | 2/2014 | Marle | A61B 6/0487 5/601 |
| 2014/0142591 A1 | 5/2014 | Alvarez et al. | |

(56) References Cited

U.S. PATENT DOCUMENTS

| | | |
|---|---|---|
| 2014/0275985 A1 | 9/2014 | Walker et al. |
| 2014/0276391 A1 | 9/2014 | Yu |
| 2014/0276647 A1 | 9/2014 | Yu |
| 2014/0276935 A1 | 9/2014 | Yu |
| 2014/0277333 A1 | 9/2014 | Lewis et al. |
| 2014/0277334 A1 | 9/2014 | Yu et al. |
| 2014/0309649 A1 | 10/2014 | Alvarez et al. |
| 2014/0350387 A1 | 11/2014 | Siewerdsen et al. |
| 2014/0357984 A1 | 12/2014 | Wallace et al. |
| 2014/0364870 A1 | 12/2014 | Alvarez et al. |
| 2014/0379000 A1 | 12/2014 | Romo et al. |
| 2015/0026889 A1* | 1/2015 | Roselius ............ A61B 6/0442 5/601 |
| 2015/0047125 A1* | 2/2015 | Bae .................... A61B 6/56 5/601 |
| 2015/0051592 A1 | 2/2015 | Kintz |
| 2015/0101442 A1 | 4/2015 | Romo |
| 2015/0119638 A1 | 4/2015 | Yu et al. |
| 2015/0164594 A1 | 6/2015 | Romo et al. |
| 2015/0164596 A1 | 6/2015 | Romo et al. |
| 2015/0335480 A1 | 11/2015 | Alvarez et al. |
| 2016/0000627 A1 | 1/2016 | Jackson et al. |
| 2016/0001038 A1 | 1/2016 | Romo et al. |
| 2016/0100896 A1 | 4/2016 | Yu |
| 2016/0235946 A1 | 8/2016 | Lewis et al. |
| 2016/0270865 A1 | 9/2016 | Landey et al. |
| 2016/0287279 A1 | 10/2016 | Bovay et al. |
| 2016/0296294 A1 | 10/2016 | Moll et al. |
| 2016/0338785 A1 | 11/2016 | Kokish et al. |
| 2016/0354582 A1 | 12/2016 | Yu et al. |
| 2016/0374541 A1 | 12/2016 | Agrawal et al. |
| 2017/0007337 A1 | 1/2017 | Dan |
| 2017/0007343 A1 | 1/2017 | Yu |
| 2017/0065364 A1 | 3/2017 | Schuh et al. |
| 2017/0065365 A1 | 3/2017 | Schuh |
| 2017/0100199 A1 | 4/2017 | Yu et al. |
| 2017/0105804 A1 | 4/2017 | Yu |
| 2017/0119413 A1 | 5/2017 | Romo |
| 2017/0119481 A1 | 5/2017 | Romo et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0215978 A1 | 8/2017 | Wallace et al. |
| 2017/0290631 A1 | 10/2017 | Lee et al. |
| 2017/0333679 A1 | 11/2017 | Jiang |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0177556 A1 | 6/2018 | Noonan |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000576 A1 | 1/2019 | Mintz et al. |
| 2019/0083183 A1 | 3/2019 | Moll et al. |
| 2019/0105776 A1 | 4/2019 | Ho et al. |
| 2019/0105785 A1 | 4/2019 | Meyer et al. |
| 2019/0107454 A1 | 4/2019 | Lin et al. |
| 2019/0110839 A1 | 4/2019 | Rafii-Tari et al. |
| 2019/0110843 A1 | 4/2019 | Ummalaneni |
| 2019/0151148 A1 | 5/2019 | Alvarez et al. |
| 2019/0167366 A1 | 6/2019 | Ummalaneni et al. |
| 2019/0175009 A1 | 6/2019 | Mintz et al. |
| 2019/0175062 A1 | 6/2019 | Rafii-Tari et al. |
| 2019/0175287 A1 | 6/2019 | Hill et al. |
| 2019/0175799 A1 | 6/2019 | Hsu et al. |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre et al. |
| 2019/0223974 A1 | 7/2019 | Romo et al. |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda et al. |
| 2019/0298465 A1 | 10/2019 | Chin et al. |
| 2019/0328213 A1 | 10/2019 | Landey et al. |
| 2019/0336238 A1 | 11/2019 | Yu et al. |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Auer |
| 2019/0380787 A1 | 12/2019 | Ye et al. |
| 2019/0380797 A1 | 12/2019 | Yu et al. |
| 2020/0000533 A1 | 1/2020 | Schuh et al. |
| 2020/0022767 A1 | 1/2020 | Hill et al. |
| 2020/0038123 A1 | 2/2020 | Graetzel et al. |
| 2020/0039086 A1 | 2/2020 | Meyer et al. |
| 2020/0046434 A1 | 2/2020 | Graetzel et al. |
| 2020/0054408 A1 | 2/2020 | Schuh et al. |
| 2020/0060516 A1 | 2/2020 | Baez, Jr. |
| 2020/0085516 A1 | 3/2020 | DeFonzo et al. |
| 2020/0093549 A1 | 3/2020 | Chin et al. |
| 2020/0093554 A1 | 3/2020 | Schuh et al. |
| 2020/0100845 A1 | 4/2020 | Julian |
| 2020/0100853 A1 | 4/2020 | Ho et al. |
| 2020/0100855 A1 | 4/2020 | Leparmentier et al. |
| 2020/0101264 A1 | 4/2020 | Jiang |
| 2020/0107894 A1 | 4/2020 | Wallace et al. |
| 2020/0121502 A1 | 4/2020 | Kintz |
| 2020/0146769 A1 | 5/2020 | Eyre et al. |
| 2020/0170720 A1 | 6/2020 | Ummalaneni |
| 2020/0171660 A1 | 6/2020 | Ho et al. |
| 2020/0188043 A1 | 6/2020 | Yu et al. |
| 2020/0197112 A1 | 6/2020 | Chin et al. |
| 2020/0206472 A1 | 7/2020 | Ma et al. |
| 2020/0217733 A1 | 7/2020 | Lin et al. |
| 2020/0222134 A1 | 7/2020 | Schuh et al. |
| 2020/0237458 A1 | 7/2020 | DeFonzo et al. |
| 2020/0261172 A1 | 8/2020 | Romo et al. |
| 2020/0268459 A1 | 8/2020 | Noonan |
| 2020/0268460 A1 | 8/2020 | Tse et al. |
| 2020/0281787 A1 | 9/2020 | Ruiz |
| 2020/0297437 A1 | 9/2020 | Schuh et al. |
| 2020/0297444 A1 | 9/2020 | Camarillo et al. |
| 2020/0305983 A1 | 10/2020 | Yampolsky et al. |
| 2020/0305989 A1 | 10/2020 | Schuh et al. |
| 2020/0305992 A1 | 10/2020 | Schuh et al. |
| 2020/0315717 A1 | 10/2020 | Bovay et al. |
| 2020/0315723 A1 | 10/2020 | Hassan et al. |
| 2020/0323596 A1 | 10/2020 | Moll et al. |
| 2020/0330167 A1 | 10/2020 | Romo et al. |
| 2020/0345216 A1 | 11/2020 | Jenkins |
| 2020/0352420 A1 | 11/2020 | Graetzel et al. |
| 2020/0360183 A1 | 11/2020 | Alvarez et al. |
| 2020/0367726 A1 | 11/2020 | Landey et al. |
| 2020/0367981 A1 | 11/2020 | Ho et al. |
| 2020/0375678 A1 | 12/2020 | Wallace et al. |

OTHER PUBLICATIONS

Advisory Action for U.S. Appl. No. 15/438,589, dated Dec. 5, 2019, 2 pages.

Advisory Action for U.S. Appl. No. 15/438,589, dated Oct. 16, 2019, 4 pages.

(56) References Cited

OTHER PUBLICATIONS

Final Rejection for U.S. Appl. No. 15/438,589, dated Sep. 21, 2020, 23 pages.
Final Rejection for U.S. Appl. No. 15/438,589, dated Sep. 24, 2021, 26 pages.
Final Rejection for U.S. Appl. No. 15/438,589, dated Sep. 9, 2019, 16 pages.
Non-Final Rejection for U.S. Appl. No. 15/438,589, dated Apr. 9, 2020, 19 pages.
Non-Final Rejection for U.S. Appl. No. 15/438,589, dated Mar. 17, 2021, 26 pages.
Non-Final Rejection for U.S. Appl. No. 15/438,589, dated Mar. 20, 2019, 13 pages.
Notice Of Allowance for U.S. Appl. No. 15/438,589, dated Jan. 3, 2022, 8 pages.
Office Action for U.S. Appl. No. 15/438,589, dated Sep. 24, 2021, 26 pages.

\* cited by examiner

FLOATING ELECTROMAGNETIC FIELD GENERATOR SYSTEM AND METHOD OF CONTROLLING THE SAME

CROSS-REFERENCE TO RELATED APPLICATIONS

This application is a continuation of U.S. patent application Ser. No. 15/438,589, filed Feb. 21, 2017, now U.S. Pat. No. 11,324,554, which claims the benefit of U.S. Provisional Patent Application Ser. No. 62/320,193 entitled "Floating Electromagnetic Field Generator System and Method of Controlling the Same," filed Apr. 8, 2016, the disclosures of which are hereby incorporated by reference in their entireties.

BACKGROUND

Field of the Invention

The field of the present application pertains to medical devices. More particularly, the field of the invention pertains to an electromagnetic tracking surgical system and a method of controlling the same.

Description of the Related Art

A surgical procedure may be performed on a patient using one or more surgical tools when the patient is placed on a surgical bed. The surgical tools may include endoscopes, catheters, ureteroscopes, or other similar devices. Endoscopy is a widely-used, minimally invasive technique for both imaging and delivering therapeutics to anatomical locations within the human body. Typically a flexible endoscope is used to deliver tools to an operative site inside the body—e.g., through small incisions or a natural orifice in the body—where a surgical procedure is to be performed. Endoscopes may have imaging, lighting and steering capabilities at the distal end of a flexible shaft enabling navigation of non-linear lumens or pathways.

SUMMARY

Examples of a floating electromagnetic (EM) field generator system are provided. The floating EM field generator system may be used to support and/or develop arms disposed next to a surgical bed so as to prevent distortion of a field generator system due to bending of the surgical bed.

The placement of field generator coils within or adjacent to a surgical bed may be used for tracking surgical tools. In particular, when a sensor associated with a surgical tool interacts with an EM field generated by the field generator coils, the interactions may be measured to determine a location of the surgical tool.

However, the determination of a location of the surgical tool is based on a calibration of the field generator coils within an initial position. If the position of the field generator coils is altered, however, such as due to bending of the surgical bed, the interactions of the surgical tool sensor with the resulting EM field may result in measurements that do not correctly reflect the location of the surgical tool.

In order to avoid inaccurate determinations of surgical tool locations, structures are provided that fully or partially decouple arms used to embed field generator coils from a surgical bed. In this way, disturbances that occur at the surgical bed, such as bending, may be partially or fully prevented from affecting the EM field generator system.

In a first aspect of the invention, two arms that are adjacent to a surgical bed may be used to embed field generator coils. The arms may be supported using a brace portion. Additionally, the arms may be partially decoupled from the surgical bed so as to prevent, or partially prevent, the bending of the surgical bed from affecting the position of the arms.

In a second aspect of the invention, a base connector that connects two hinged arms, that are adjacent to a surgical bed, may rest against a base portion that is even with or below a level of a surgical bed. In this way, the base connector of the hinged arms may be in contact with the base portion independent of the placement or bending of the adjacent surgical bed. Additionally, the arms may be decoupled from the surgical bed so as to prevent, or partially prevent, the bending of the surgical bed from affecting the position of the arms.

In a third aspect of the invention, an intermediate connector that connects two hinged arms, that are adjacent to a surgical bed, may rest against a base portion that is even with or below a level of a surgical bed. In this way, the intermediate connector of the hinged arms may be in contact with the base portion independent of the placement or bending of the adjacent surgical bed. Additionally, the arms may be decoupled from the surgical bed so as to prevent, or partially prevent, the bending of the surgical bed from affecting the position of the arms.

In another aspect of the invention, a floating electromagnetic field generator system is provided. The system comprises a surgical bed portion. The system also comprises a brace component disposed within the surgical bed portion. Additionally, the system comprises a first arm that is attached to the brace component. The first arm may be positioned adjacent to the surgical bed portion. Additionally, the first arm may have at least one field generator coil embedded therein. The system also comprises a second arm that is attached to the brace component. The second arm may be positioned adjacent to the surgical bed portion. Additionally, the second arm may have at least one field generator coil embedded therein. The second arm may be positioned parallel to the first arm.

In some embodiments, the brace component is a circular brace component. In some embodiments, the first and the second arm are independent of movement the surgical bed portion. In further embodiments, the first and the second arm are independent of bending of the surgical bed portion.

In some embodiments, the first arm and the second arm are attached to the brace component using a hinge. In some embodiments, the first arm and the second arm are additionally attached using a connecting component. In further embodiments, the connecting component is a base connecting component. In additional further embodiments, the connecting component is an intermediate connecting component. In some embodiments, the intermediate connecting component has a width of three inches. In some embodiments, the intermediate connecting component has a width of five inches. In some embodiments, the intermediate connecting component has a width of between three inches and five inches.

In a further aspect of the invention, a floating electromagnetic field generator system is provided. The system comprises a first surgical bed portion that is connected to, and movable with respect to, a second bed portion. The system also comprises a brace component connected to the first surgical bed portion. Additionally, the system comprises a first arm that is attached to the brace component. The first arm may be positioned adjacent to the surgical bed portion, and the first arm having at least one field generator coil connected thereto. The system also comprises a second arm that is attached to the brace component. The second arm may be positioned adjacent to the surgical bed portion. Additionally, the second arm may have at least one field generator coil connected thereto.

In some embodiments, the first and second arm are partially independent of movement of the surgical bed portion. In some embodiments, the first and second arm are independent of movement of the surgical bed portion. In further embodiments, the first and the second arm are independent of bending of the surgical bed portion.

In some embodiments, each of the first arm and second arm have a plurality of field generator coils connected thereto. Additionally, in some embodiments, each of the first arm and the second arm has a plurality of field generator coils detachably attached thereto.

Another aspect of the invention provides a floating electromagnetic field generator system is provided. The system comprises a surgical bed portion. The system also comprises a brace component disposed within the surgical bed portion. Additionally, the system comprises a first hinged arm that is attached to the brace component, the first hinged arm positioned adjacent to the surgical bed portion, and the first hinged arm having at least one field generator coil embedded therein. The system also comprises a second hinged arm that is attached to the brace component, the second hinged arm positioned adjacent to the surgical bed portion, and the second hinged arm having at least one field generator coil embedded therein, the second hinged arm positioned parallel to the first hinged arm. Further, the system comprises a base connecting component that connects the first hinged arm and the second hinged arm.

In some embodiments, wherein the base connecting component is at a same level as the surgical bed. In some embodiments, the base connecting component is below the surgical bed. In some embodiments, the first and the second arm are independent of movement the surgical bed portion. In some embodiments, the first and the second arm are independent of bending of the surgical bed portion.

A further aspect of the invention provides a floating electromagnetic field generator system. The system comprises a surgical bed portion. The system also comprises a brace component disposed within the surgical bed portion. Additionally, the system comprises a first arm that is attached to the brace component, the first arm positioned adjacent to the surgical bed portion, and the first arm having at least one field generator coil embedded therein. The system further comprises a second arm that is attached to the brace component, the second arm positioned adjacent to the surgical bed portion, and the second arm having at least one field generator coil embedded therein, wherein the second arm is connected to the first arm using an intermediate connecting component.

In some embodiments, the intermediate connecting component is at a same level as the surgical bed. In some embodiments, the intermediate connecting component is below the surgical bed. In some embodiments, the first arm and the second arm are attached to the brace component using a hinge. In some embodiments, each of the first arm and second arm have a plurality of field generator coils connected thereto. In further embodiments, each of the first arm and second arm have a plurality of field generator coils detachably attached thereto. Additionally, in some embodiments, each of the first arm and the second arm have a plurality of field generator coils embedded within.

It shall be understood that different aspects of the invention can be appreciated individually, collectively, or in combination with each other. Other objects and features of the present invention will become apparent by a review of the specification, claims, and appended figures.

BRIEF DESCRIPTION OF THE DRAWINGS

The invention will be described, by way of example, and with reference to the accompanying drawings, in which.

DETAILED DESCRIPTION

Figure 1:
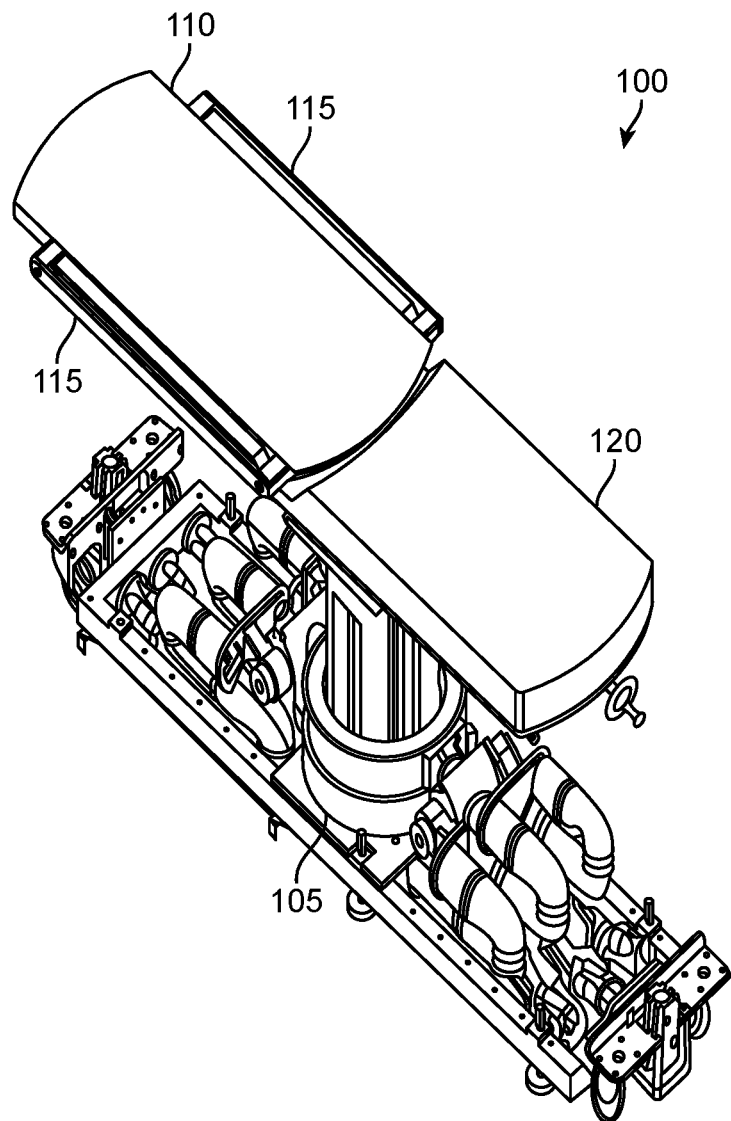
FIG. 1 illustrates a perspective view of a surgical bed system having arms for embedding electromagnetic field generator coils, in accordance with some embodiments.

Although certain preferred embodiments and examples are disclosed below, the inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

Floating electromagnetic (EM) field generator systems for tracking a surgical tool relative to a surgical bed are provided. The floating EM field generator system may comprise arms. In particular, the arms that are next to a surgical bed may have EM field generator coils embedded therein. The EM field generator coils may be used to generate an EM field over at least a portion of the surgical bed. Additionally, the arms may be within a structure that is independent, or at least partially independent, from weight-bearing portions of the surgical bed. As such, in examples, floating EM field generator systems may be used to decouple the orientation of field generator coils from bending that may occur on a surgical bed.

In examples, an EM field generator may be used as one navigational component of a surgical tool tracking system that includes visual component and/or a fluoroscopic component. Additionally, systems provided that utilize three navigational components may be more accurate in tracking a surgical tool than navigational systems that only use one or two navigational components.

When using an EM field generator tracking system, a sensor associated with a surgical tool may be tracked based on interactions of the sensor with an electromagnetic field. In particular, a sensor associated with a surgical tool may be tracked when voltage is induced within a sensor coil that is placed within the electromagnetic field. In examples, the system provided may be used for alternating current (AC) EM tracking. In other examples, the system may be used for direct current (DC) EM tracking.

The electromagnetic field may be calibrated having a predetermined precision along a length of a surgical bed in the system. Small variations in position can be detected based on the sensor interaction with the electromagnetic field. The positional variations can have a spatial resolution of less than about 10 mm, 9 mm, 8 mm, 7 mm, 6 mm, 5 mm, 4 mm, 3 mm, 2 mm, or 1 mm. In some cases, the spatial resolution may be greater than about 10 mm. However, once a set of field generator coils are embedded, it is beneficial that the field generator coils remain in the same position, or at least the same position relative to the other field generator coils. If the field generator coils do not stay in the same position, the calibration of the field generator coils may be invalid, and the determined location of the sensor associated with the surgical tool may be incorrect.

Accordingly, the system may comprise a plurality of field generator coils embedded within arms that are associated with a surgical bed. The arms having the field generator coils embedded within may be disposed with respect to the surgical bed. In some examples, the field generator coils embedded within the arms may be placed with respect to, but decoupled from, the surgical bed. In this way, the field generator coils within the arms may be protected, or partially protected, from disturbances from the surgical bed.

Each field generator coil, or subset of field generator coils, may be configured to generate a magnetic field within a control volume. The control volume may be static. Alternatively, the control volume may be capable of changing dynamically (e.g., time-variable). The system may further comprise a position sensor disposed on a portion of the surgical tool. The position sensor may be configured to generate a sensor signal in response to the magnetic field when the position sensor is located inside the control volume. Additionally, the system may comprise an EM system controller configured to selectively activate one or more of the subsets of field generator coils based on the sensor signal. Further, the system may also comprise a plurality of calibration files that correspond to each individual configuration of activated coils.

In some cases, a physician may need to know the spatial information of an endoscope relative to the patient's body, using the surgical bed as a datum. The spatial information may include a spatial position and/or orientation of the endoscope in a three-dimensional coordinate system. One or more sensors may be attached to the endoscope to determine the spatial information. The sensors may include electromagnetic (EM) sensors configured to detect the spatial information of the endoscope, as well as movement of the endoscope, within the environment of the surgical bed. The EM sensors may be used in conjunction with a set of field generator coils that are disposed at or next to the surgical bed. The field generator coils may be configured to produce a calibrated (known) electromagnetic (EM) field over a working volume above and close to the surgical bed. The working volume may be defined as a three-dimensional space above the surgical bed where a portion of the patient's body is located. A region of interest on the patient's body (e.g., where a surgical procedure is to be performed) may be disposed within the working volume. When the endoscope moves within the working volume, the interaction of the EM sensors with the EM field results in electrical signals (e.g., voltages) being generated. The spatial information and/or movement of the endoscope can be determined by analyzing the electrical signals.

Current state-of-the-art field generator coils may be provided in different configurations. For example, in some cases, a flat configuration of field generator coils may be placed in a surgical bed directly under a patient. Alternatively, a box configuration of field generator coils may be placed externally on a side of the surgical bed or positioned above/over the patient. Optionally, a window configuration of field generator coils may be positioned under the surgical bed or under the patient. However, each of the above configurations has certain deficiencies. For example, use of fluoroscopy may be limited in the flat configuration because the generator coils constitute radio-opaque objects/regions that can obstruct fluoroscopic imaging (e.g., X-ray imaging). The box configuration may interfere with a physician's access to a patient since the coils are placed externally on the side of the surgical bed or positioned above/over the patient. In the window configuration, the positioning of coils under the surgical bed may result in mechanical and/or electromagnetic interference with other devices (e.g., motors for actuating the bed, linear actuator drives, radio-frequency (RF) circuits, etc.) that are also disposed under the surgical bed. Additionally, the positioning of coils under the patient may require an overall thickness of the bed to be increased, which results in larger form factor and higher manufacturing costs.

Additional drawbacks of one or more of the above coil configurations may include limited range of use. For example, the field generators in the above configurations typically generate a working volume of about 0.5 m×0.5 m×0.5 m, which is often insufficient to encompass a length or a width of a patient's body. In some instances, the surgical procedure may involve different parts of the patient's body that are spaced outside of the typical 0.5 m×0.5 m×0.5 m working volume. In those instances, movement of the coils around the surgical bed may be required, which may increase the mechanical complexity of the system and interfere with the physician's access to the patient.

Accordingly, it would be beneficial to have a floating EM field generator system and a method of controlling the system that provides improved navigation, ergonomics, and usability. A floating electromagnetic (EM) field generator system for tracking a surgical tool may be provided in accordance with another aspect of the invention. The system may comprise a plurality of subsets of field generator coils embedded within arms that are disposed with respect to a surgical bed. Each subset of field generator coils may be configured to generate a magnetic field within a control volume. A central portion of the surgical bed may be fluoroscopically transparent. The system may also comprise a position sensor disposed on a portion of the surgical tool. The position sensor may be configured to generate a sensor signal in response to the magnetic field when the position sensor is located inside the control volume. The system may further comprise an EM system controller configured to activate one or more of the subsets of field generator coils.

1. Overview

A floating electromagnetic field generator surgical system is provided in which field generator coils are embedded within arms of a surgical bed system. In examples, the field generator coils are placed in arms that are decoupled from movement and/or weight bearing on a bed portion of the surgical bed system. As a patient rests on a bed portion of the surgical bed, the arms containing the field generator coils may stay rigid. In other examples, the arms may be movable while keeping in steady position relative to each other. Using methods and systems discussed herein, field generator coils within arms of the surgical bed system may be relatively stable independent of a weight of a patient on a bed portion of the surgical bed system.

The placement of field generator coils in the disclosed configurations allows for unobstructed use of fluoroscopic imaging, and allows a physician to easily access the patient during a surgical procedure. Unlike some conventional systems, the field generator coils in the disclosed EM tracking surgical systems do not interfere with the physician's access to the patient. The integration of thick field generator coils within arms of the surgical bed system may also help to make beds thicker, which may allow for swivel to occur.

The disclosed configurations of field generator coils as embedded in arms of the surgical bed system also allow a plurality of EM fields to be selectively activated within different working volumes above the surgical bed. The selective activation of EM fields within the different working volumes can prevent interfering EM fields from being generated, and can reduce EM interference between the field generator coils and other devices. Reduction in EM interference can improve the accuracy and sensitivity with which a surgical tool (e.g., an endoscope having one or more EM sensors) can be tracked within the different working volumes above the surgical bed. Additionally, the disclosed configurations of field generator coils can extend the range of use of the system by a physician, since the working volumes can be configured to extend along a length of the surgical bed or in other configurations, depending on the requirements and complexity of the surgical procedure.

In additional examples, tracking of a surgical tool can be facilitated by activating different subsets of field generator coils. In examples, different subsets of field generator coils may be activated depending on the location of the surgical procedure relative to the surgical bed. Additionally, in examples, coils outside of the active subset(s) of field generator coils are inactive, thereby preventing interfering EM fields from being generated. In some examples, the working volumes above adjacent subsets of field generator coils may overlap so as to form a continuous global working volume along the length of the surgical bed. In addition, the calibration files needs to be swapped for each configuration.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

2. Views of Floating EM Field Generator System

FIG. 1 illustrates a perspective view of a surgical bed system having arms for embedding electromagnetic field generators, in accordance with some embodiments. In particular, FIG. 1 illustrates a surgical bed 100 positioned on a base component 105. Surgical bed 100 may have a first portion 110 and a second portion 120, the first portion 110 having arms 115 that may be used to embed field generator coils (not shown). In examples, arms 115 may be connected and structurally supported using a brace component.

The brace component may help to support the arms so as to prevent bending and/or twisting of the arms when disturbances may occur further down the surgical bed. In examples, disturbances may occur in the surgical bed due to bending of the surgical bed due to the weight of a patient, hanging equipment, physician interaction, etc. In examples, bending and/or twisting of the arms may modify the EM field that is generated using field generator coils, thereby making the tracking of a surgical tool within the EM field less accurate. As such, decoupling the bending moment and/or lessening disruption of the surgical bed from the field generator coils embedded in arms of the surgical bed may improve accuracy of a tracking system that utilizes the EM field generated by the floating EM field generator system.

Figure 2:
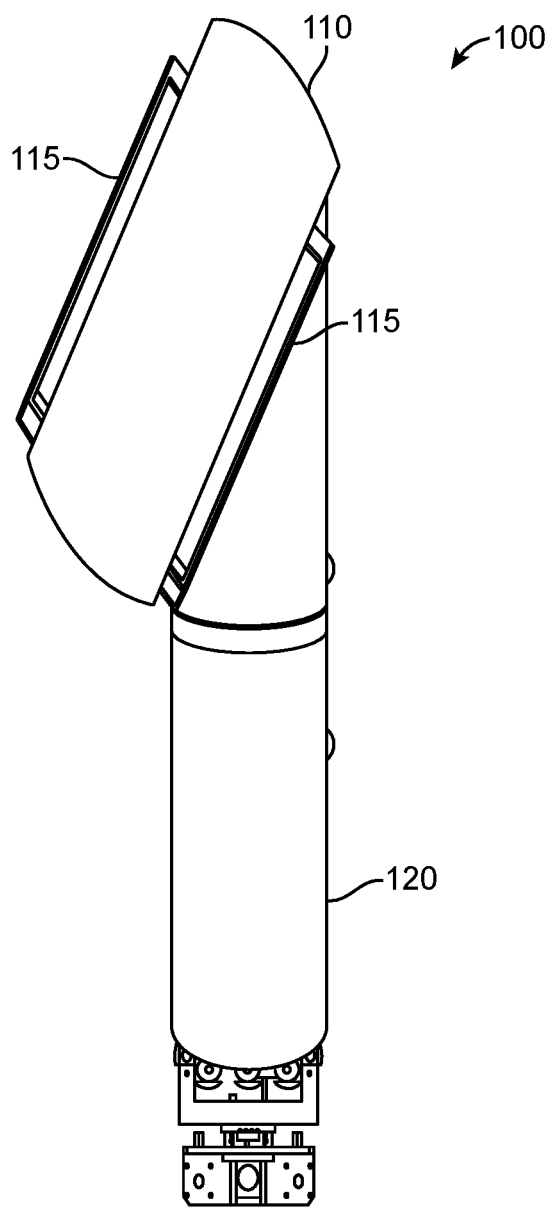
FIG. 2 illustrates an overhead view of a surgical bed system having rigid arms for embedding electromagnetic field generator coils, in accordance with some embodiments.

FIG. 2 illustrates an overhead view of a surgical bed system of FIG. 1 having rigid arms for embedding electromagnetic field generators, in accordance with some embodiments. In particular, surgical bed system 100 as shown in FIG. 2 illustrates another view of first portion 110, second portion 120, and arms 115 as presented in FIG. 1. As seen in FIG. 2, arms 115 may be placed in rows that are parallel with respect to one another. There may be two sets of calibration, the device calibration and registration. In examples, registration occurs when arms 115 may be at different levels with respect to one another and relative to the patient. At times when registration is off, the device can still perform as expected. In examples, registration may be done with arms 115 at various positions relative to the patient. However, if the coils are displaced from their relative positions with respect to one another at the time of device calibration, the device may not perform as expected.

Figure 3:
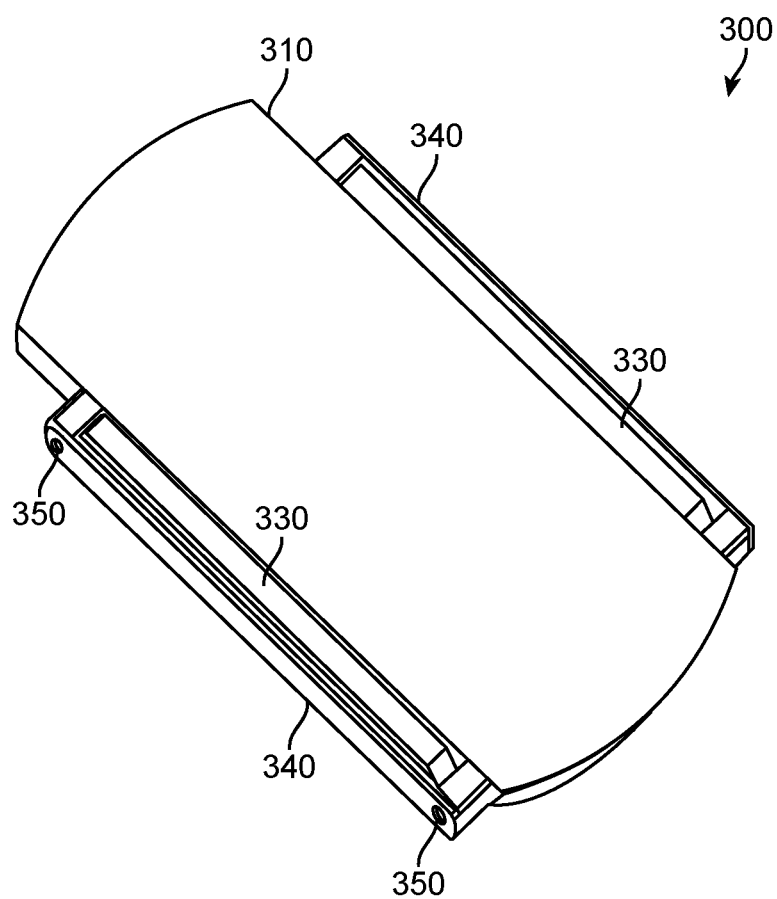
FIG. 3 illustrates a swivel-top portion of a surgical bed system having rigidly placed arms for embedding electromagnetic field generator coils, in accordance with some embodiments.

FIG. 3 illustrates a swivel-top portion 300 of a surgical bed system having rigidly placed arms for embedding electromagnetic field generator coils, in accordance with some embodiments. The swivel top provides the ability to swivel the torso portion of the platform away from the longitudinal axis, allowing for positioning the patient's groin over the side of the platform so that open access is provided for the surgical arms. In particular, FIG. 3 illustrates a bed component 310, a brace (not shown), arms 330, bed rails 340, and securing components 350. As seen in FIG. 3, the position of arms 330 relative to one another is maintained based on rigidly connecting arms 330 to a base structure, such as a brace. The brace may be made from a stainless steel bearing block embedded into structural foam and firmly rooted in place with resin, and/or may be completely encapsulated in Carbon Fiber. In some examples, this is the stiffest point of the bed that can be approximated to have zero deflection.

Figure 4:
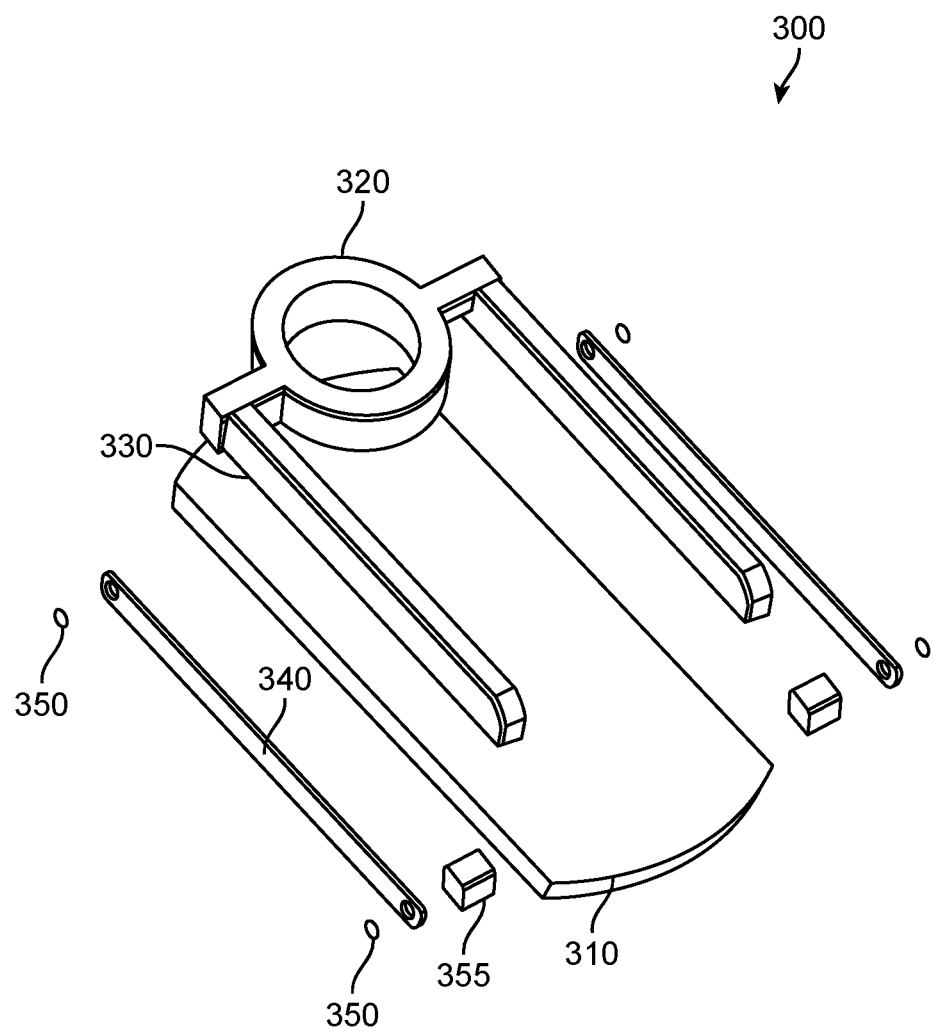
FIG. 4 illustrates an exploded view of a swivel-top portion of a surgical bed system having rigidly placed arms for embedding electromagnetic field generator coils, in accordance with some embodiments.

FIG. 4 illustrates an exploded view of a swivel-top portion of a surgical bed system having rigidly placed arms for embedding electromagnetic field generator coils, in accordance with some embodiments. In particular, FIG. 4 illustrates an exploded view of a swivel-top portion 300 as seen in FIG. 3. As such, FIG. 4 illustrates a bed component 310, a brace 320, arms 330, bed rails 340, and securing components 350. Additionally, FIG. 4 illustrates spacers 355.

As seen in FIG. 4, arms 330 may individually be attached to brace 320. In examples, brace 320 and arms 330 may be formed from a single component. In additional examples, arms 330 may be used to embed one or more field generator coils (not shown). Further, arms 330 may be decoupled from bed 310 so as to allow bed 310 to bend without placing a direct pressure on arms 330. In examples, bed 310 may bend due to the weight of a patient. The weight of the patient may also affect brace 320. In some examples, the structure of brace 320 may be reinforced by the brace material and/or the circular component of the brace 320 so as to prevent bending within arms 330 attached to brace 320. In further examples, arms 330 may be moved in a direction associated with the surgical bed in response to the weight of a patient. However, the rigid material of arms 330 and/or brace 320 may be used to keep the arms 330 rigid even as they are displaced through space. In this way, arms 330 may move downwards, but may have a rigid structure with respect to one another.

Figure 5:
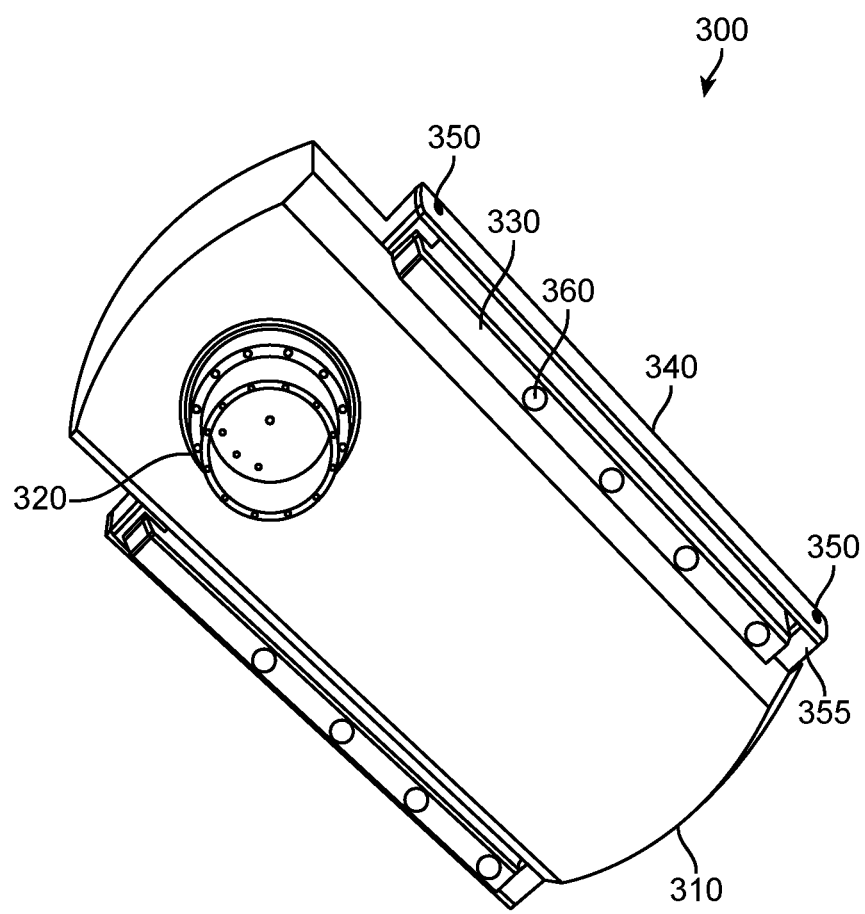
FIG. 5 illustrates a perspective view of underneath a swivel-top portion of a surgical bed system having rigidly placed arms with electromagnetic field generator coils embedded therein, in accordance with some embodiments.

FIG. 5 illustrates a perspective view of underneath a swivel-top portion of a surgical bed system having rigidly placed arms with electromagnetic field generator coils embedded therein, in accordance with some embodiments. In particular, FIG. 5 illustrates an exploded view of a swivel-top portion 300 as seen in FIG. 3. As such, FIG. 5 illustrates a bed component 310, a brace 320, arms 330, bed rails 340, securing components 350, and spacers 355. Additionally, FIG. 5 illustrates field generator coils 360. As seen in FIG. 5, field generator coils 360 may be placed at an equal distance apart from one another. In other examples, field generator coils 360 may be placed at unequal distances from one another. In some examples, the distance between field generator coils 360 may be due to design of the arms 330. As seen in FIG. 5, field generator coils 360 may be embedded in arms 330 and, as such, may be placed with respect to bed component 310 based on a placement of arms 330 with respect to bed component 310.

Figure 6:
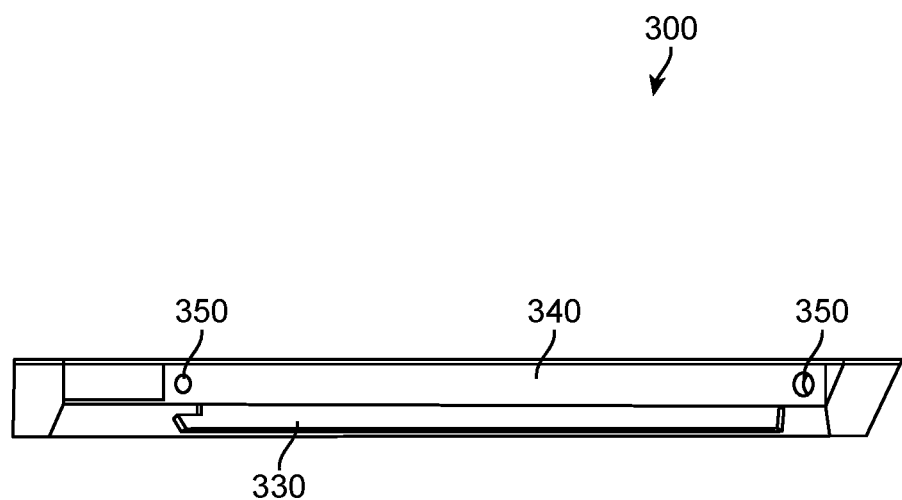
FIG. 6 illustrates a side view of a first position of a swivel-top portion of a surgical bed system having rigidly placed arms for embedding electromagnetic field generator coils, in accordance with some embodiments.

FIG. 6 illustrates a side view of a first position of a swivel-top portion 300 of a surgical bed system having rigidly placed arms for embedding electromagnetic field generator coils, in accordance with some embodiments. Additionally, FIG. 7 illustrates a side view of a second position of a swivel-top portion of a surgical bed system having rigidly placed arms for embedding electromagnetic field generator coils, in accordance with some embodiments.

Figure 7:
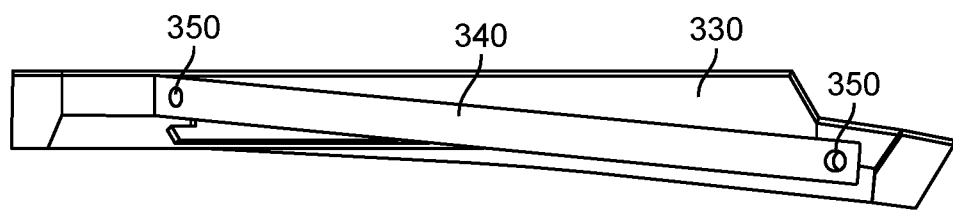
FIG. 7 illustrates a side view of a second position of a swivel-top portion of a surgical bed system having rigidly placed arms for embedding electromagnetic field generator coils, in accordance with some embodiments.

As seen in FIGS. 6 and 7, as a bed component and bed rails 340 move downwards from a first position to a second position, arms 330 may stay stable. In particular, arms 330 may stay rigid independent of the movement and/or bending of bed component based on the bracing of arms 330 using brace 320.

Figure 8:
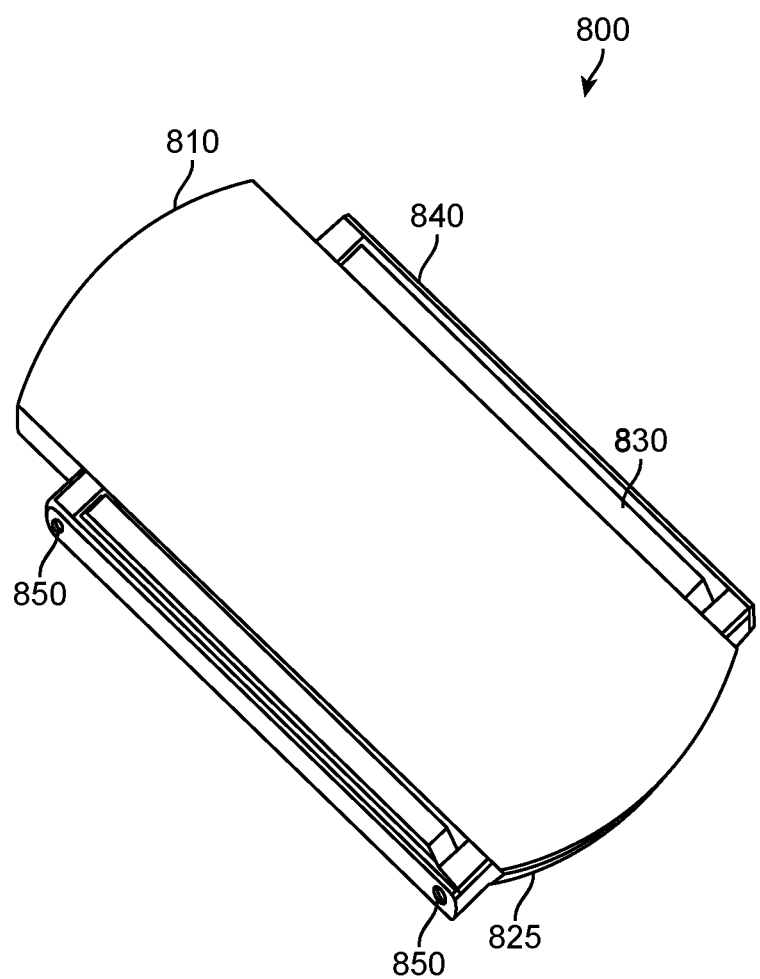
FIG. 8 illustrates a swivel-top portion of a surgical bed system having hinged arms for embedding electromagnetic field generator coils, in accordance with some embodiments.

FIG. 8 illustrates a swivel-top portion 800 of a surgical bed system having hinged arms for embedding electromagnetic field generator coils, in accordance with some embodiments. In particular, FIG. 8 illustrates a bed component 810, a brace (not shown), arms 830, bed rails 840, and securing components 850. As seen in FIG. 8, the position of arms 830 relative to one another is maintained based on connecting arms 830 to a base structure 820, as well as connecting arms 830 using a base connecting component 825. By using base connecting component 825, the arms' hinge-like movement of arms 830 may be equal such that the arms 830 maintain their position with respect to each other. In examples, where arms maintain a stable position with respect to each other, the characteristics of a field generated using field generator coils within the arms 830 may also be stabilized.

Figure 9:
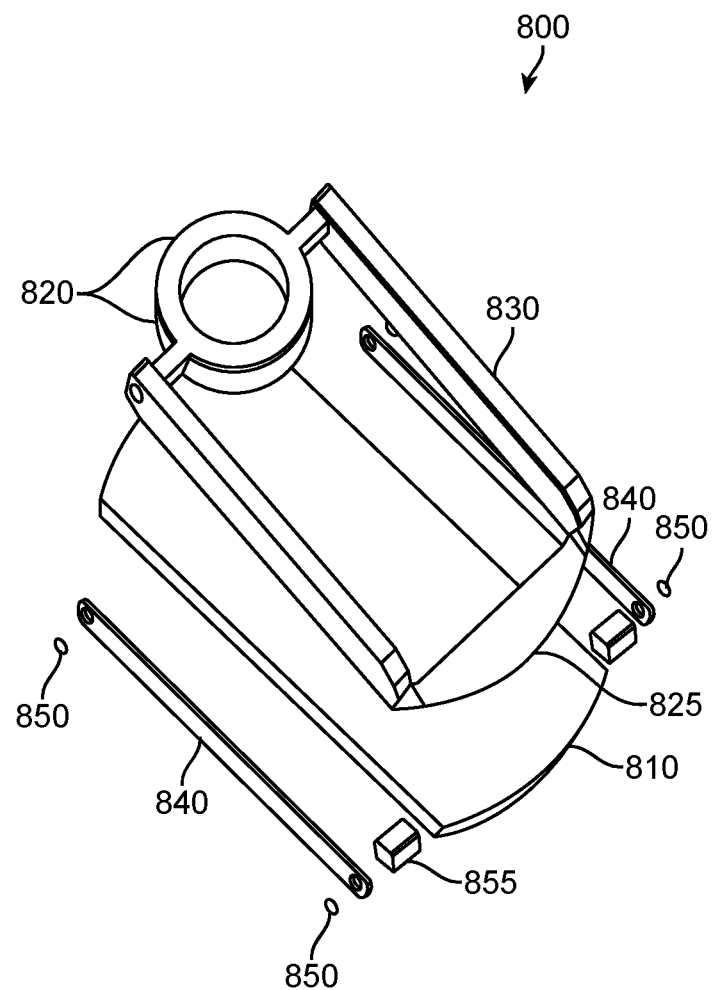
FIG. 9 illustrates an exploded view of a swivel-top portion of a surgical bed system having hinged arms for embedding electromagnetic field generator coils, in accordance with some embodiments.

FIG. 9 illustrates an exploded view of a swivel-top portion of a surgical bed system having hinged arms for embedding electromagnetic field generator coils, in accordance with some embodiments. In particular, FIG. 9 illustrates an exploded view of a swivel-top portion 800 as seen in FIG. 8. As such, FIG. 9 illustrates a bed component 810, a brace 820, a base connecting component 825, arms 830, bed rails 840, and securing components 850. Additionally, FIG. 9 illustrates spacers 855.

Figure 10:
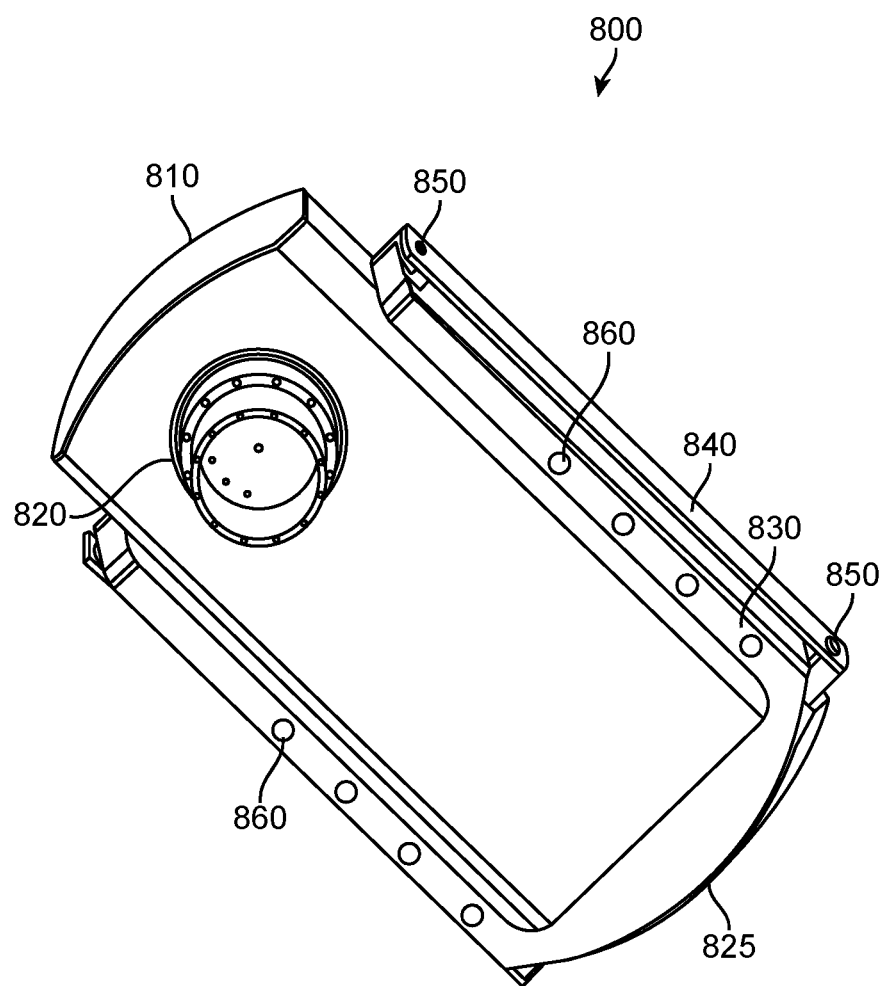
FIG. 10 illustrates a perspective view of underneath a swivel-top portion of a surgical bed system having hinged arms for embedding electromagnetic field generator coils, in accordance with some embodiments.

FIG. 10 illustrates a perspective view of underneath a swivel-top portion 800 of a surgical bed system having hinged arms for embedding electromagnetic field generator coils, in accordance with some embodiments. As such, FIG. 10 illustrates a bed component 810, a brace 820, a base connecting component 825, arms 830, bed rails 840, securing components 850, and spacers 855. Additionally, FIG. 10 illustrates field generator coils 860 (e.g., within arms 830). As seen in FIG. 10, field generator coils may be placed at an equal distance apart from one another. In other examples, field generator coils may be placed at unequal distances from one another. In some examples, the distance between field generator coils, such as field generator coils 860, may be due to design of the arms, such as arms 830. In some examples, the distance between the field generator coils may be based on a surgical procedure to be performed. As seen in FIG. 10, field generator coils may be embedded in arms 830 and, as such, may be placed with respect to bed component 810 based on a placement of arms 830 with respect to bed component 810.

Figure 11:
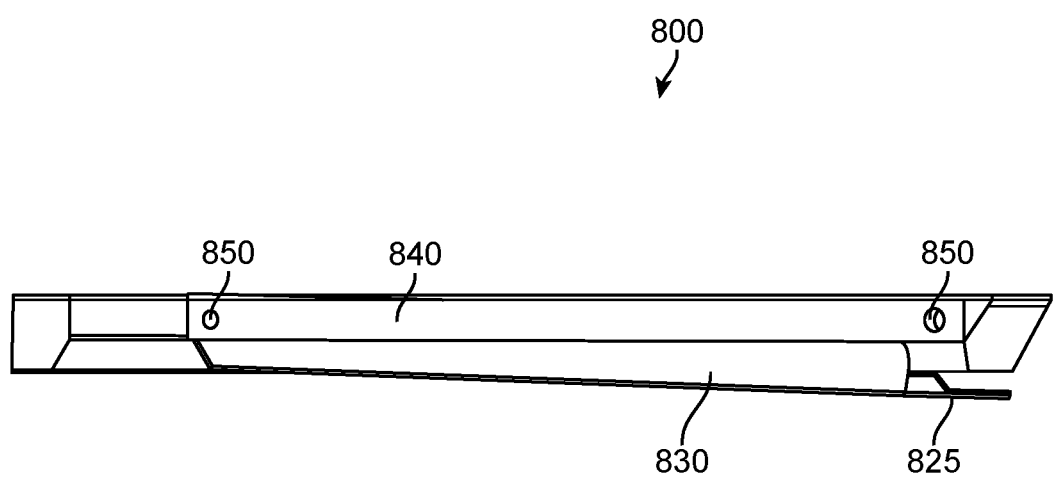
FIG. 11 illustrates a side view of a first position of a swivel-top portion of a surgical bed system having hinged arms for embedding electromagnetic field generator coils, in accordance with some embodiments.
Figure 12:
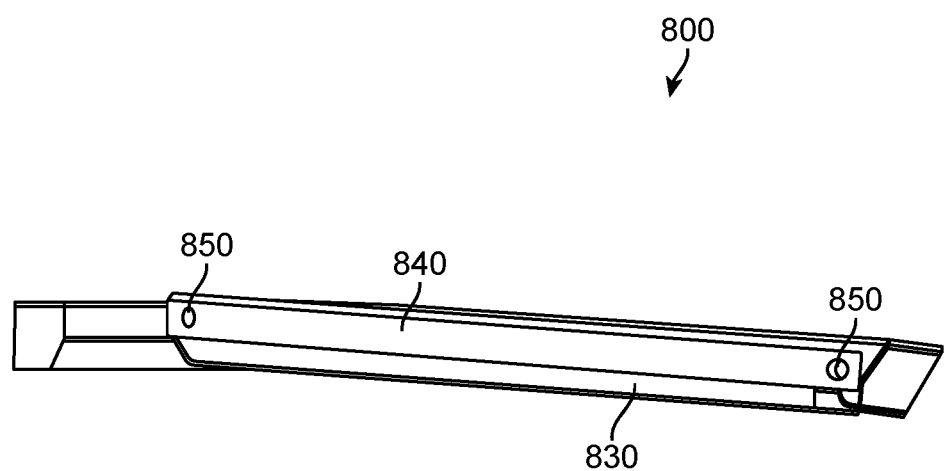
FIG. 12 illustrates a side view of a second position of a swivel-top portion of a surgical bed system having hinged arms for embedding electromagnetic field generator coils, in accordance with some embodiments.

FIG. 11 illustrates a side view of a first position of a swivel-top portion 800 of a surgical bed system having hinged arms for embedding electromagnetic field generator coils, in accordance with some embodiments. Additionally, FIG. 12 illustrates a side view of a second position of a swivel-top portion of a surgical bed system having hinged arms for embedding electromagnetic field generator coils, in accordance with some embodiments. As seen in FIGS. 11 and 12, as bed component 810 moves downwards from a first position to a second position, arms 830 may stay stable at a position that is lower or level with bed component 810. Either way, arms 830 may stay in a same position independent of movement of bed portion 810. In examples, arms 830 and base connecting component 825 may rest against a further support, such as a base, to further support arms 830 and base connecting component 825.

Figure 13:
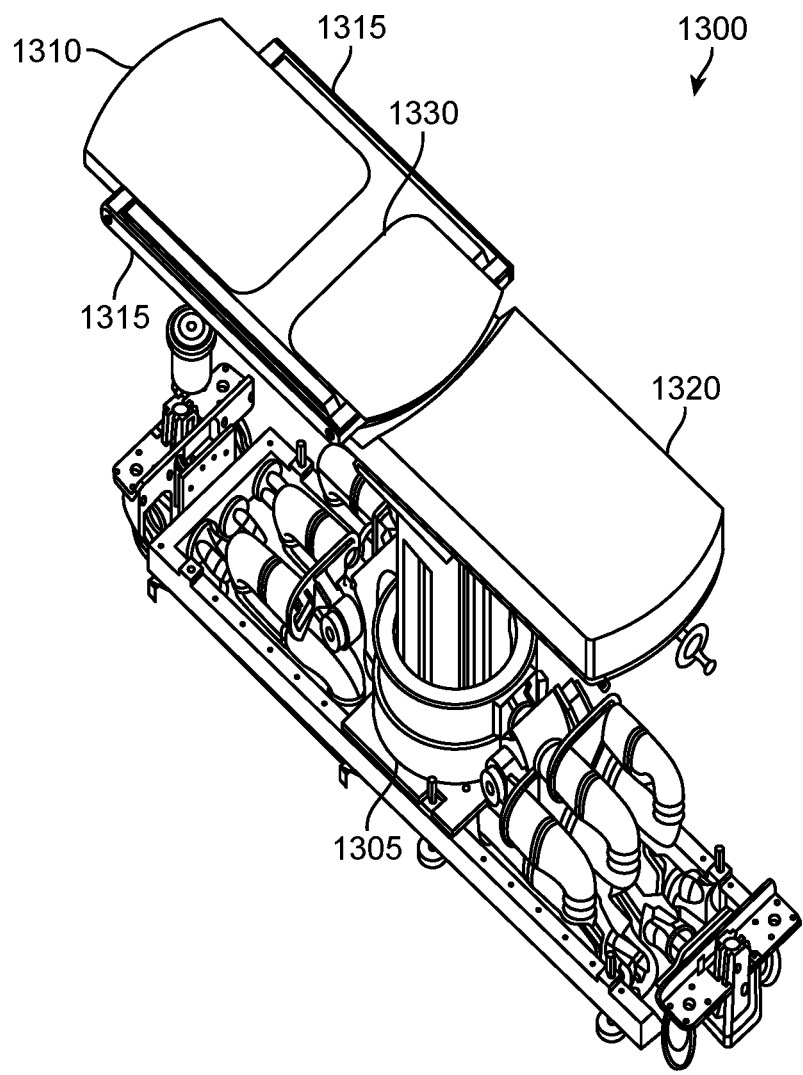
FIG. 13 illustrates a perspective view of a surgical bed system having arms for embedding electromagnetic field generator coils, the arms connected using a median brace, in accordance with some embodiments.

FIG. 13 illustrates a perspective view of a surgical bed system having arms for embedding electromagnetic field generator coils, the arms connected using a median brace, in accordance with some embodiments. In particular, FIG. 13 illustrates a surgical bed 1300 positioned on a base component 1305. Surgical bed 1300 may have a first portion 1310 and a second portion 1320, the first portion 1310 having arms 1315 that may be used to embed field generator coils (not shown). In examples, arms 1315 may be connected and structurally supported using an intermediate brace component 1330.

Figure 14:
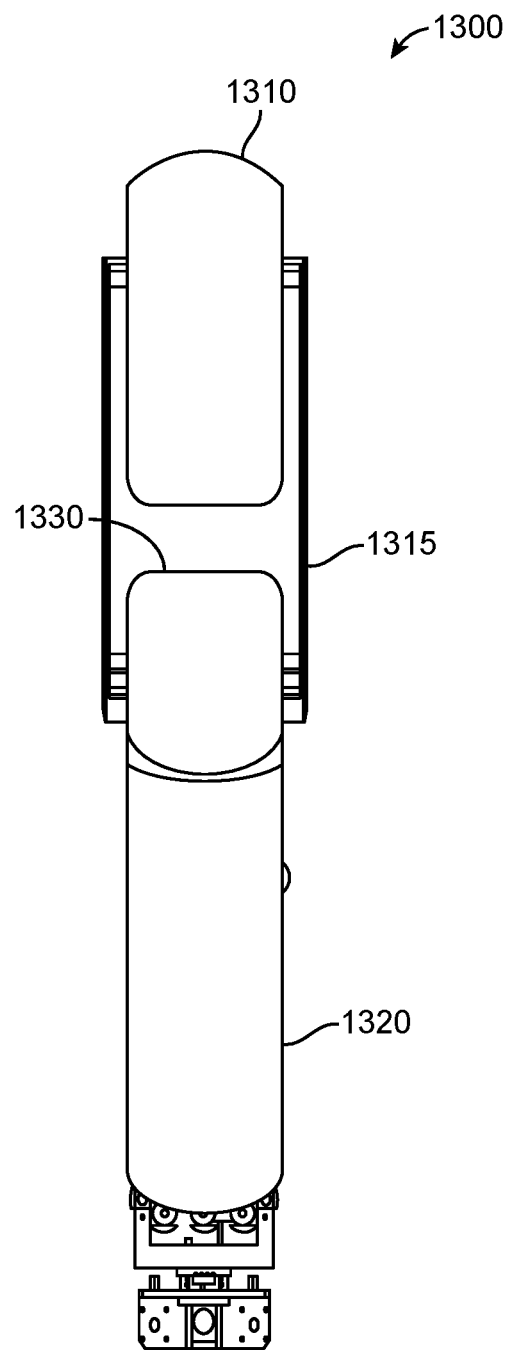
FIG. 14 illustrates an overhead view of a surgical bed system having arms connected using a median brace for embedding electromagnetic field generator coils, in accordance with some embodiments.

FIG. 14 illustrates an overhead view of a surgical bed system having arms connected using a median brace for embedding electromagnetic field generator coils, in accordance with some embodiments. In particular, surgical bed 1300 as shown in FIG. 14 illustrates another view of first portion 1310, second portion 1320, and arms 1315 as presented in FIG. 13. As seen in FIG. 14, arms 1315 may be placed in rows that are parallel with respect to one another. Additionally, arms 1315 are attached using an intermediate brace component 1330. The structural support of arms 1315 using an intermediate brace component 1330 may be used to prevent bending of arms 1315 when a patient is on bed 1300.

Figure 15:
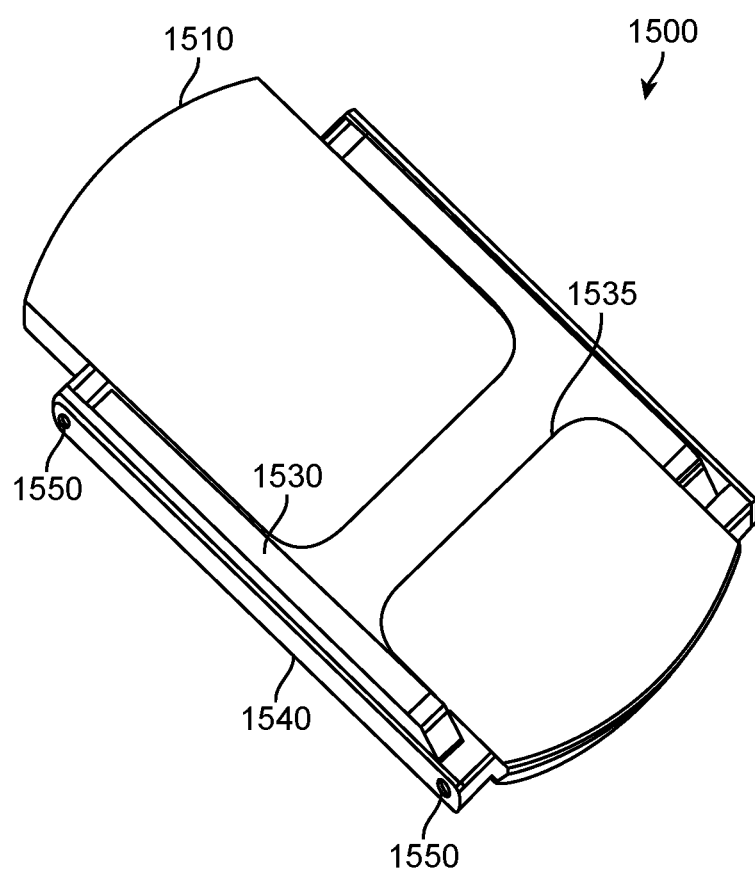
FIG. 15 illustrates a swivel-top portion of a surgical bed system having arms for embedding electromagnetic field generator coils, the arms connected using a median brace, in accordance with some embodiments.

FIG. 15 illustrates a swivel-top portion 1500 of a surgical bed system having arms for embedding electromagnetic field generator coils, the arms connected using a median brace, in accordance with some embodiments. In particular, FIG. 15 illustrates a bed component 1510, arms 1530, intermediate brace component 1535, bed rails 1540, and securing components 1550. As seen in FIG. 15, the position of arms 1530 relative to one another is maintained based on rigidly connecting arms 1530 to intermediate brace component 1535. In examples, intermediate brace component 1535 may have a band that is three inches wide. In some examples, the band of intermediate brace component 1535 is less than three inches wide, and in some examples, the band of intermediate brace component 1535 is more than three inches wide. In examples, the band of intermediate brace component 1535 may be less than an inch; may be an inch; may be 1.5 inches; may be 2 inches; may be 2.5 inches; may be 3 inches; may be 3.5 inches; may be 4 inches; may be 4.5 inches; may be 5 inches; or may be more than 5 inches.

Figure 16:
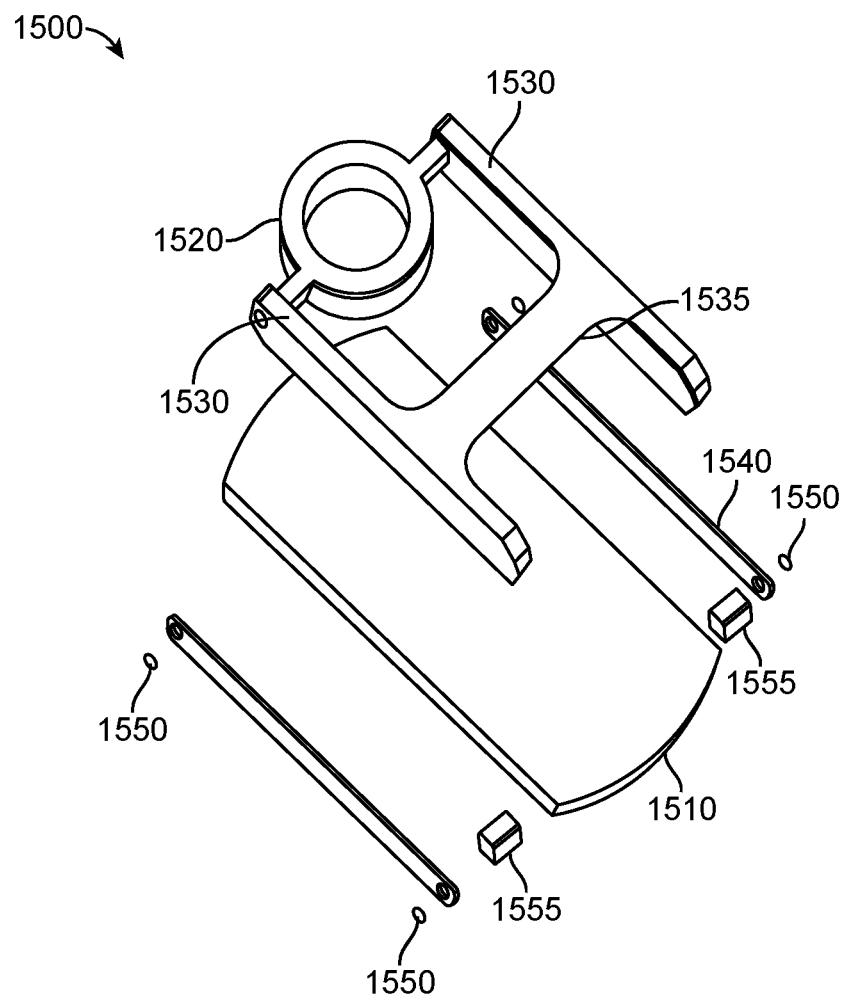
FIG. 16 illustrates an exploded view of a swivel-top portion of a surgical bed system having arms for embedding electromagnetic field generator coils, the arms connected using a median brace, in accordance with some embodiments.

FIG. 16 illustrates an exploded view of a swivel-top portion of a surgical bed system having arms for embedding electromagnetic field generator coils, the arms connected using a median brace, in accordance with some embodiments. In particular, FIG. 16 illustrates an exploded view of a swivel-top portion 1500 as seen in FIG. 15. As such, FIG. 16 illustrates a bed component 1510, circular brace component 1520, arms 1530, intermediate brace component 1535, bed rails 1540, and securing components 1550. Additionally, FIG. 16 illustrates spacers 1555.

As seen in FIG. 16, arms 1530 may be joined through their attachment to intermediate brace component 1535. Additionally, arms 1530 may be joined to another, circular base component 1520 within bed component 1510. In examples, circular brace component 1520, arms 1530, and intermediate brace component 1535 may be formed from a single component. In additional examples, arms 1530 may be used to embed one or more field generator coils (not shown). Further, arms 1530 may be decoupled from bed component 1510 so as to allow bed component 1510 to bend without placing a direct pressure on arms 1530. In examples, bed component 1510 may bend due to the weight of a patient. The weight of the patient may also affect circular brace component 1520 and/or intermediate brace component 1535, but the structure of circular brace component 1520 and/or intermediate brace component 1535 may be reinforced by the brace material and/or the shape of the brace component so as to prevent bending within arms 1530 attached to brace components 1520 and/or 1535. In further examples, arms 1530 may be moved in a direction associated with the surgical bed in response to the weight of a patient. However, the rigid material of circular brace component 1520, arms 1530, and/or intermediate brace component 1535 may be used to keep the arms 1530 rigid even as they are displaced through space. In this way, arms 1530 may move downwards, but may have a rigid structure with respect to one another.

Figure 17:
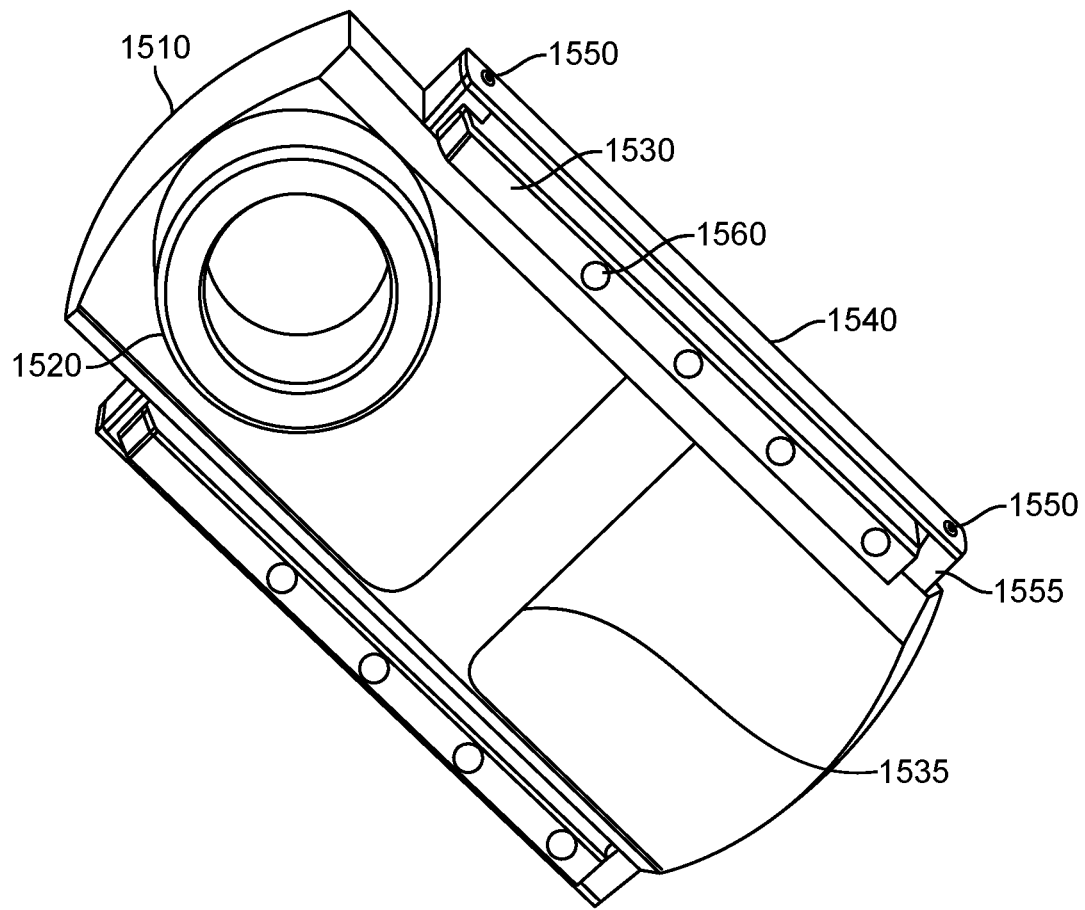
FIG. 17 illustrates a perspective view of underneath a swivel-top portion of a surgical bed system having arms with electromagnetic field generator coils embedded therein, the arms connected using a median brace, in accordance with some embodiments.

FIG. 17 illustrates a perspective view of underneath a swivel-top portion of a surgical bed system having arms with electromagnetic field generator coils embedded therein, the arms connected using a median brace, in accordance with some embodiments. As such, FIG. 17 illustrates a bed component 1510, a brace 1520, arms 1530, an intermediate brace component 1535, bed rails 1540, securing components 1550, and spacers 1555. Additionally, FIG. 17 illustrates field generator coils 1560. As seen in FIG. 17, field generator coils 1560 may be placed at an equal distance apart from one another. In other examples, field generator coils 1560 may be placed at unequal distances from one another. In some examples, the distance between field generator coils 1560 may be due to design of the arms 1530. In some examples, the distance between the field generator coils 1560 may be based on a surgical procedure to be performed. As seen in FIG. 17, field generator coils 1560 may be embedded in arms 1530 and, as such, may be placed with respect to bed component 1510 based on a placement of arms 1530 with respect to bed component 1510.

Figure 18:
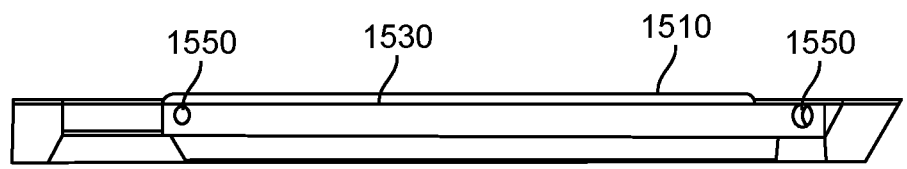
FIG. 18 illustrates a side view of a first position of a swivel-top portion of a surgical bed system having arms for embedding electromagnetic field generator coils, the arms connected using a median brace, in accordance with some embodiments.
Figure 19:
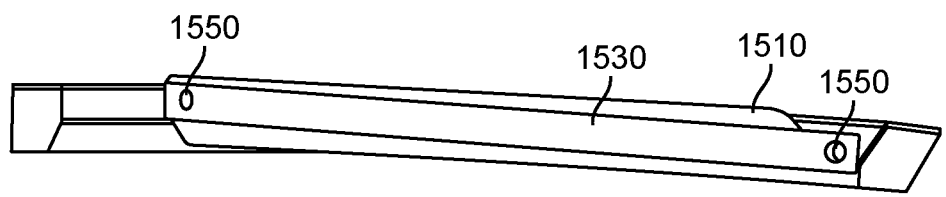
FIG. 19 illustrates a side view of a second position of a swivel-top portion of a surgical bed system having arms for embedding electromagnetic field generator coils, the arms connected using a median brace, in accordance with some embodiments.

FIG. 18 illustrates a side view of a first position of a swivel-top portion of a surgical bed system having arms for embedding electromagnetic field generator coils, the arms connected using a median brace, in accordance with some embodiments. FIG. 19 illustrates a side view of a second position of a swivel-top portion of a surgical bed system having arms for embedding electromagnetic field generator coils, the arms connected using a median brace, in accordance with some embodiments. As seen in FIGS. 18 and 19, as bed component 1510 moves downwards from a first position to a second position, arms 1530 may stay stable. In particular, arms 1530 may stay rigid independent of the movement and/or bending of surgical bed 1510 based on the bracing of arms 1530 using circular brace component (not shown) and intermediate brace component (not shown). Additionally, FIGS. 18 and 19 illustrate securing components 1550.

System Components

Figure 20:
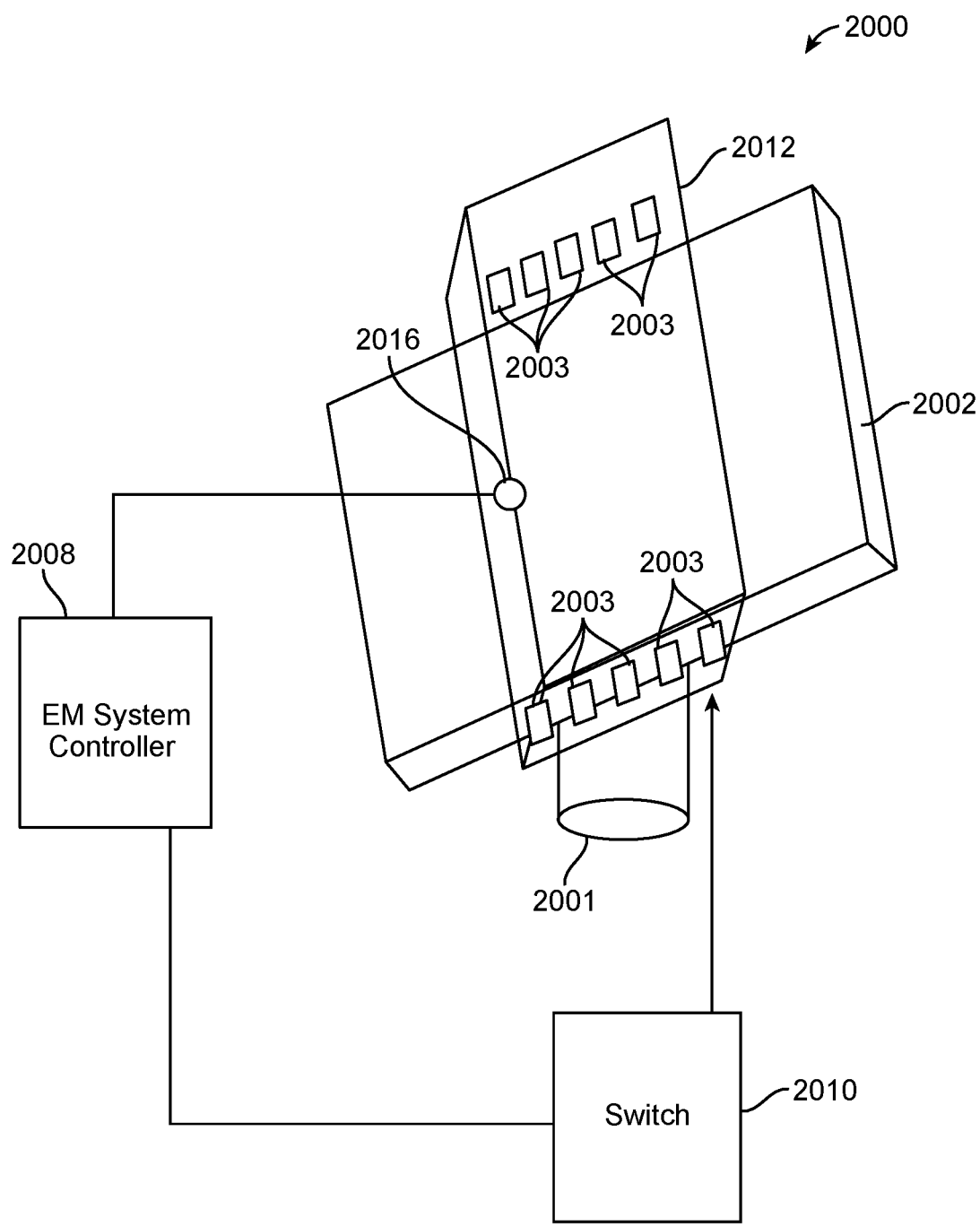
FIG. 20 illustrates a schematic of a floating electromagnetic (EM) field generator system that generates a single field, in accordance with some embodiments.

FIG. 20 illustrates a schematic of a floating EM field generator system 2000 that generates a single field 2012, in accordance with some embodiments. As shown in FIG. 20, the floating EM field generator system 2000 may also comprise a surgical bed 2002 that rests on a base 2001, a plurality of field generator coils 2003, an EM system controller 2008, a switch module 2010, and a position sensor 2016.

The surgical bed 2002 may be configured to support a patient. A physician may perform a surgical procedure on the patient while the patient is placed on the surgical bed 2002. In some embodiments, the surgical bed 2002 may comprise multiple sections that are movable relative to one another. In those embodiments, the patient's body can be moved into different positions by moving different sections of the surgical bed 2002 relative to one another. Alternatively, the surgical bed 2002 may be formed monolithically as a single rigid structure.

The plurality of field generator coils 2003 may be embedded or integrated within arms 2014 associated with the surgical bed 2002. For example, as shown in FIG. 20, the plurality of field generator coils 2003 may be embedded within arms (not shown) associated with the surgical bed 2002 in two rows. The rows may extend parallel to each other along the edge of the surgical bed 2002. As previously mentioned, the field generator coils 2003 constitute radio-opaque objects/regions. Accordingly, the placement of the field generator coils 2003 within arms next to surgical bed 2002 can allow unobstructed use of fluoroscopy to image the patient's body during a surgical procedure.

Figure 21:
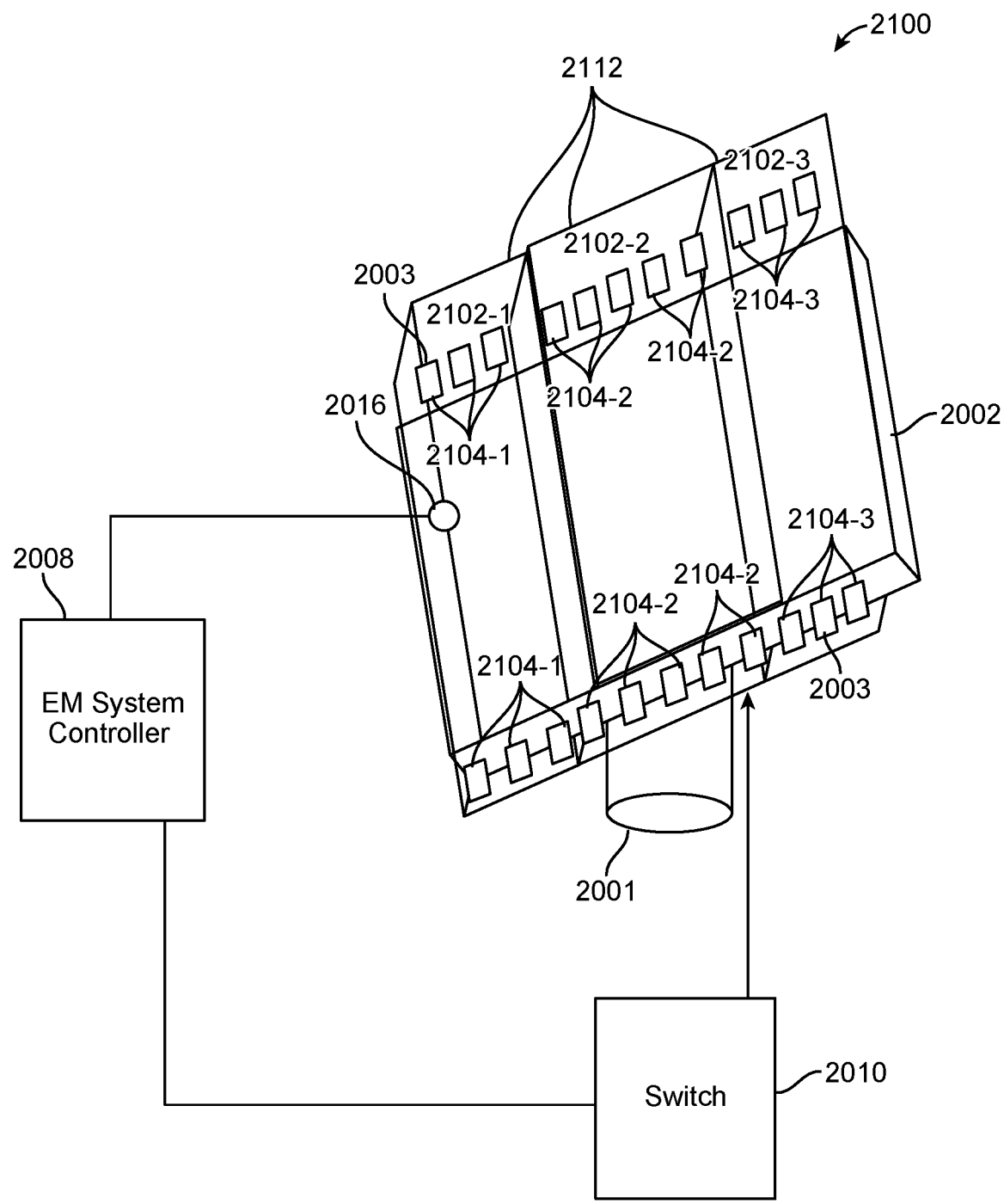
FIG. 21 illustrates a schematic of a floating electromagnetic (EM) field generator system that generates multiple fields, in accordance with some embodiments.

In some examples, a plurality of working volumes 2112 may be generated using subsets of field generator coils 2104. This is shown in FIG. 21, which illustrates a schematic of a floating EM field generator system that generates multiple fields, in accordance with some embodiments. As seen in FIG. 21, the plurality of working volumes 2112 may include a first working volume 2102-1, a second working volume 2102-2, and a third working volume 2102-3. Each working volume 2112 may be associated with a subset of field generator coils, and may be disposed directly above the respective subset of field generator coils. For example, the first working volume 2102-1 may be disposed directly above the first subset of field generator coils 2104-1, the second working volume 2102-2 may be disposed directly above the second subset of field generator coils 2104-2, and the third working volume 2102-3 may be disposed directly above the third subset of field generator coils 2104-3.

The plurality of field generator coils 2003 may include, and can be grouped into, subsets as field generator coils 2104. For example, as shown in FIG. 21, the field generator coils 2003 may include a first subset of field generator coils 2104-1, a second subset of field generator coils 2104-2, and a third subset of field generator coils 2104-3. Although three subsets are illustrated in FIG. 21, it should be noted that the invention is not limited thereto, and that any number of subsets of field generator coils may be contemplated. In examples, 2, 3, 4, 5, 6, 7, 8, 9, 10, or more than 10 subsets of field generator coils may be used.

Each subset of field generator coils 2104 may comprise a number of field generator coils. In FIG. 21, each subset of field generator coils 2104-1, 2104-2, and 2104-3 may comprise six, ten, or six field generator coils, respectively. However, each subset of field generator coils need not be limited to six field generator coils. In some embodiments, a subset of field generator coils may comprise more than six field generator coils. For example, a subset of field generator coils may comprise 7, 8, 9, 10, 11, 12, 13, 14, 15, 16, 17, 18, 19, 20, 25, 30, 35, 40, or more than 40 field generator coils. In other embodiments, a subset of field generator coils may comprise six or less generator coils. For examples, a subset of field generator coils may comprise 1, 2, 3, 4, 5, or 6 field generator coils. In some embodiments, different subsets of field generator coils may comprise different numbers of field generator coils. Any number of field generator coils within each subset, and between different subsets, may be contemplated.

The field generator coils within each subset may be fixed in place relative to one another. For example, the field generator coils may be spaced apart by a predetermined distance and/or at a predefined pitch along the edges of the surgical bed 2002. Additionally, the field generator coils may be nominally fixed relative to the surgical bed 2002 in a global coordinate system. Any portion of the surgical bed 2002 may serve as an origin of the global coordinate system. In some embodiments, a datum point that lies substantially above a center portion of the surgical bed 2002 may serve as the origin of the global coordinate system. In those embodiments, the positions of the field generator coils may be defined relative to the datum point.

The EM system controller 2008 may be configured to provide electrical current pulses to the field generator coils 2003 to generate an EM field over the respective working volume 2112 above each subset of field generator coils 2104. The EM system controller 2008 can selectively activate (power on) different subsets of field generator coils 2104 to generate EM fields in different working volumes 2112 by controlling one or more switches in the switch module 2010. Electrical current pulses may be provided from the EM system controller 2008 to the different subsets of field generator coils 2104 via one or more switches in the switch module 2010.

The switches may include electronic switches such as power MOSFETs, solid state relays, power transistors, and/or insulated gate bipolar transistors (IGBTs). Different types of electronic switches may be provided for controlling current to a subset of field generator coils. An electronic switch may utilize solid state electronics to control current flow. In some instances, an electronic switch may have no moving parts and/or may not utilize an electro-mechanical device (e.g., traditional relays or switches with moving parts). In some instances, electrons or other charge carriers of the electronic switch may be confined to a solid state device. The electronic switch may optionally have a binary state (e.g., switched-on or switched-off). The electronic switches may be used to control current flow to the subsets of field generator coils. The operation of switches to selectively activate one or more subsets of field generator coils is described with reference to FIG. 23, below.

The EM system controller 2008 can control the switches to activate: (1) the first subset of field generator coils 2104-1 to generate an EM field in the first working volume 2102-1, (2) the second subset of field generator coils 2104-2 to generate an EM field in the second working volume 2102-2, and/or (3) the third subset of field generator coils 2104-3 to generate an EM field in the third working volume 2102-3. In examples, the subsets of field generator coils may be activated simultaneously. In some examples, the subsets of field generator coils may be activated sequentially. For example, in some embodiments, the EM system controller 2008 can simultaneously activate all three subsets of field generator coils 2104 to create three separate EM fields in the respective working volumes 2112. Alternatively, the EM system controller 2008 can sequentially activate the first, second, and third subsets of field generator coils 2104-1, 2104-2, and 2104-3 to sequentially generate EM fields in the first, second, and third working volumes 2102-1, 2102-2, and 2102-3.

The EM system controller 2008 can be configured to activate one or more subsets of field generator coils without activating one or more other subsets of field generator coils. For example, in some embodiments, the EM system controller 2008 can activate only the first subset of field generator coils 2104-1 without activating the second and third subsets of field generator coils 2104-2 and 2104-3. Similarly, the EM system controller 2008 can activate only the second subset of field generator coils 2104-2 without activating the first and third subsets of field generator coils 2104-1 and 2104-3. Likewise, the EM system controller 2008 can activate only the third subset of field generator coils 2104-3 without activating the first and second subsets of field generator coils 2104-1 and 2104-2. In some cases, the EM system controller 2008 can activate the first and second subsets of field generator coils 2104-1 and 2104-2 without activating the third subset of field generator coils 2104-3. In other cases, the EM system controller 2008 can activate the second and third subsets of field generator coils 2104-2 and 2104-3 without activating the first subset of field generator coils 2104-1. Optionally, the EM system controller 108 can activate the first and third subsets of field generator coils 2104-1 and 2104-3 without activating the second subset of field generator coils 2104-2. Additional combinations (of the activation) of different subsets of field generator coils may be contemplated.

As previously described, the EM system controller 2008 can sequentially activate the first, second, and third subsets of field generator coils 2104-1, 2104-2, and 2104-3. In some embodiments, all three subsets of field generator coils may continue to be powered on after they have been sequentially activated. For example, the first subset of field generator coils 2104-1 may continue to be powered on after the second subset of field generator coils 2104-2 has been activated. The first and second subsets of field generator coils 2104-1 and 2104-2 may continue to be powered on after the third subset of field generator coils 2104-3 has been activated. Alternatively, in some embodiments, the first subset of field generator coils 2104-1 may be powered off after the second subset of field generator coils 2104-2 has been activated, and the second subset of field generator coils 2104-2 may be powered off after the third subset of field generator coils 2104-3 has been activated.

In some embodiments, the EM system controller 2008 may be located on the surgical bed 2002, for example on a base configured to support the surgical bed 2002. In some embodiments, the EM system controller 2008 may be located remotely from the surgical bed 2002. For example, the EM system controller 2008 may be disposed in a remote server that is in communication with the subsets of field generator coils 2004 and the switch module 2010. The EM system controller 2008 may be software and/or hardware components included with the server. The server can have one or more processors and at least one memory for storing program instructions. The processor(s) can be a single or multiple microprocessors, field programmable gate arrays (FPGAs), or digital signal processors (DSPs) capable of executing particular sets of instructions. Computer-readable instructions can be stored on a tangible non-transitory computer-readable medium, such as a flexible disk, a hard disk, a CD-ROM (compact disk-read only memory), and MO (magneto-optical), a DVD-ROM (digital versatile disk-read only memory), a DVD RAM (digital versatile disk-random access memory), or a semiconductor memory. Alternatively, the program instructions can be implemented in hardware components or combinations of hardware and software such as, for example, ASICs, special purpose computers, or general purpose computers.

The EM system controller 2008 may also be provided at any other type of external device (e.g., a remote controller for controlling the surgical bed 2002 and/or a surgical tool, any movable object or non-movable object, etc.). In some instances, the EM system controller 2008 may be distributed on a cloud computing infrastructure. The EM system controller 2008 may reside in different locations where the EM system controller 2008 is capable of controlling the switch module 2010 and selectively activating one or more subsets of field generator coils 2004 based on the spatial information of the position sensor 2016.

The position sensor 2016 may be disposed in or on a portion of a surgical tool. For example, in some embodiments, the position sensor 2016 may be disposed at a distal end of the surgical tool. Examples of surgical tools may include endoscopes, catheters, ureteroscopes, forceps, different types of scopes, or other similar devices or surgical accessories.

A position sensor, such as position sensor 2016, may be configured to generate an electrical signal (voltage or current signal) in response to EM fields generated field generator coils. Position sensor 2016 may be an EM sensor. As position sensor 2016 moves within a control volume 2012, the interaction of the position sensor 2016 with the EM field within the control volume 2012 may cause electrical signals to be generated. The electrical signals may vary as the position sensor 2016 moves between different locations within a control volume 2012. Additionally, electrical signals may vary as the position sensor 2016 moves between different control volumes. The EM system controller 2008 may be configured to receive electrical signals from the position sensor 2016. Additionally, the EM system controller 2008 may analyze the signals to compute a local position of the sensor 2016. The local position of the sensor 2016 may be computed relative to a local coordinate system. The local coordinate system may be defined at an active set of field generator coils corresponding to the control volume 2012 in which the position sensor 2016 is located.

The EM system controller 2008 may be further configured to compute a global position of the sensor 2016 relative to a global coordinate system. The global coordinate system may be defined at the surgical bed 2002 (e.g., above a center portion of the surgical bed 2002). The global position of the sensor 2016 may be computed based on: (1) the local position of the sensor 2016 within the control volume 2012 above an active set of field generator coils, and (2) the position of the active set of field generator coils relative to the surgical bed 2002. The global position of the sensor 2016 may be used to determine a position of a surgical tool relative to a patient on the surgical bed 2002.

The EM system controller 2008 may be configured to control the switch module 2010 based on one or more inputs. The control of the switch module 2010, and the selective activation of one or more field generator coils, may be manual and/or automatic.

In some embodiments, the EM system controller 2008 may control the switch module 2010 based on a user input corresponding to a selection of a region (or working volume 2112) of the surgical bed 2002 where tracking of a surgical tool is desired. For example, a physician may plan to perform a surgical procedure on a patient in a region within the first working volume 2112-1. Accordingly, the physician or the physician's assistant may provide an input to the EM system controller 2008 to activate the first subset of field generator coils 2104-1, so that movement of the surgical tool can be tracked within the first control volume via the position sensor 2016.

In some embodiments, the EM system controller 2008 may control the switch module 2010 based on an initialization input. The initialization input may cause the EM system controller 2008 to control the switch module 2010 to sequentially activate (cycle through) the subsets of field generator coils 2104, so as to determine: (1) whether the position sensor 2016 is present in any of the control volumes 2112, (2) in which control volume 2112 the position sensor 2016 is located if the position sensor 2016 is detected, and (3) the position of the sensor 2016 within the detected control volume 2112. Accordingly, the EM system controller 2008 can control the switch module 2010 to activate the subset of field generator coils 2104 corresponding to the control volume 2112 in which the position sensor 2016 is located, without activating the other subsets of field generator coils.

During the sequential activation (cycling) of the subsets of field generator coils 2104, the local position of the sensor 2016 relative to the local coordinate system of the working volume 2112 (where the sensor 2016 is located) may be determined. The local position of the sensor 2016 may be determined based on a distance between the sensor 2016 and a reference point in the local coordinate system. The reference point may lie anywhere in the local coordinate system. For example, in some embodiments, the reference point may be at an origin of the local coordinate system. One or more subsets of field generator coils 2104 may be activated based on the distance between the sensor 2016 and the reference point.

For example, when the reference point is an origin of a local coordinate system that is defined at a center of a control volume 2112, and the position sensor 2016 is located at or near the reference point, only the subset of field generator coils corresponding to that control volume 2112 may be activated. Conversely, when the position sensor 2016 is located far away from the reference point such that the sensor 2016 is proximate to another control volume 2112, adjacent subsets of field generator coils 2104 corresponding to both control volumes 2112 may be activated. It should be noted that the local coordinate system need not be defined at the center of a control volume 2112. In some other instances, the local coordinate system may be defined near an edge or corner of a control volume 2112. Any placement of the reference point and/or the local coordinate system within a control volume 2112 may be contemplated.

In some embodiments, the local position of the sensor 2016 may be determined based on distances between the sensor 2016 and a plurality of reference points in different local coordinate systems. The different local coordinate systems may lie in different control volumes 2012. The EM system controller 2008 may be configured to determine a minimum distance from those distances, and activate a subset of field generator coils 2104 corresponding to the control volume 2012 based on the minimum distance.

During a surgical procedure, the EM system controller 2008 may be configured to track the position and/or movement of the sensor 2016 within a control volume 2112 corresponding to an active subset of field generator coils 2104. As the position sensor 2016 moves between adjacent control volumes 2112, different subsets of field generator coils 2104 may be selectively activated to ensure that the sensor 2016 is continuously tracked, while at the same time reducing EM field interference effects.

3. Closed-Loop Positional and Speed Feedback

Figure 22:
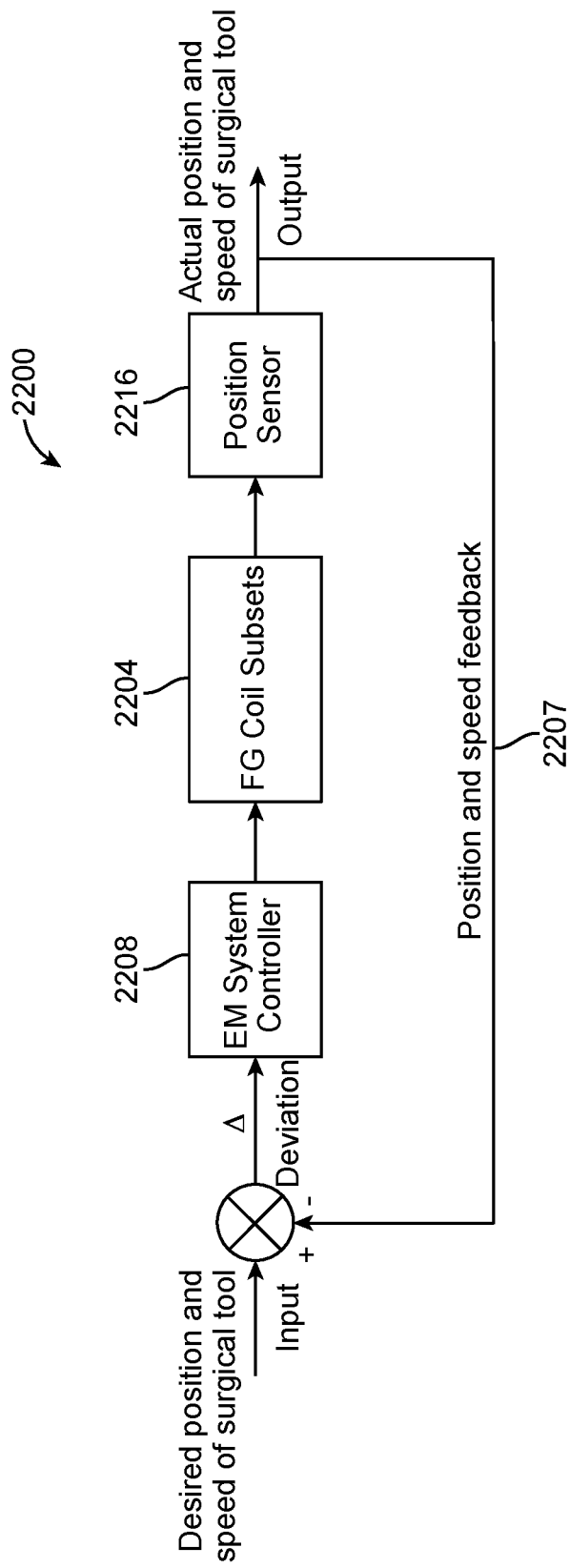
FIG. 22 illustrates a block diagram of a closed-loop control EM tracking surgical system, in accordance with some embodiments.

FIG. 22 illustrates a block diagram of a closed-loop control EM tracking surgical system, in accordance with some embodiments. As shown in FIG. 22, a closed-loop control EM tracking surgical system 2200 may comprise an EM system controller 2208, a plurality of subsets of field generator coils 1 through n, represented as 2204, and a position sensor 2216 operably connected via a feedback loop 2207. Any number (n) of subsets of field generator coils 2204 may be contemplated, and may depend in part on the strength of each subset of field generator coils 2204 and/or a size (e.g., length and width) of a surgical bed (e.g., surgical bed 102 of FIG. 1).

In FIG. 22, a surgical tool may be automatically controlled using one or more robotic arms that are in operable communication with the EM system controller 2208. The EM system controller 2208 may be configured to track and control the position and/or movement of the surgical tool, and selectively activate one or more subsets of field generator coils 2204, based on positional and speed feedback of the position sensor 2216 as the sensor 2216 moves between different control volumes (e.g., control volumes 2112 of FIG. 21).

As shown in FIG. 22, an input may be initially provided to the EM tracking surgical system 2200. The input may comprise a desired position and/or speed of a surgical tool. The position and/or speed of the surgical tool may be controlled using the one or more robotic arms. The EM system controller 2208 may be configured to activate one or more subsets of field generator coils 2204, and to determine a control volume (e.g., control volume 2012 of FIG. 20) in which the position sensor 2216 is located. Once the control volume has been determined, the subset of field generator coils 2204 corresponding to that control volume may be activated while the other subsets of field generator coils 2204 may be powered off. As previously described, the selective activation of different subsets of field generator coils 2204 can reduce EM field interference effects. The position and/or movement of the sensor 2216 may be determined based on the interaction of the sensor 2216 with the EM field within the control volume. The actual position and/or speed of the surgical tool may be determined based on the position and/or movement of the sensor 2216, and may be compared against the input to determine an amount of deviation A (if any) from the desired position and/or speed of the surgical tool. The EM system controller 2208 may be configured to adjust the actual position and/or speed of the surgical tool (via the one or more robotic arms) based on the amount of deviation.

4. Switching Circuit

Figure 23:
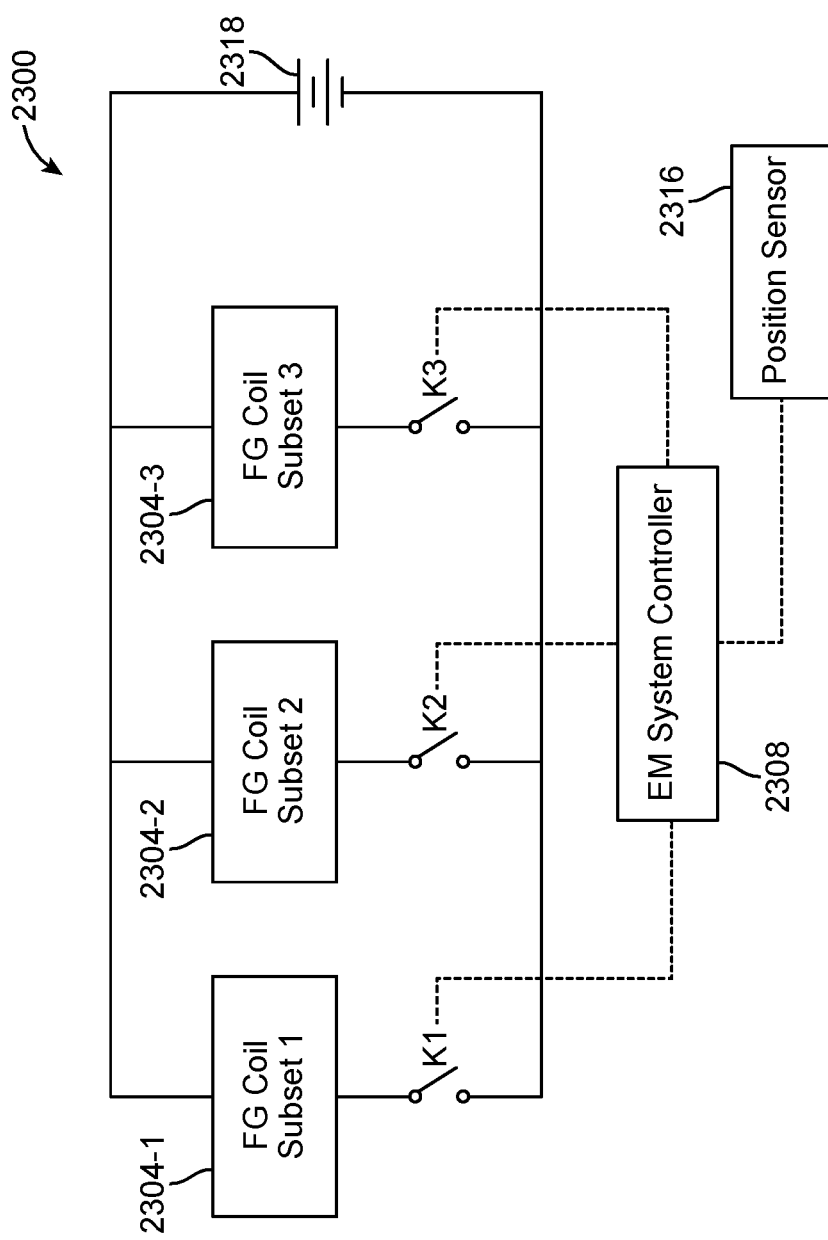
FIG. 23 illustrates a schematic circuit diagram of an EM tracking surgical system, in accordance with some embodiments.

FIG. 23 illustrates a schematic circuit diagram of an EM tracking surgical system, in accordance with some embodiments. As shown in FIG. 23, an EM tracking surgical system 2300 may comprise a plurality of subsets of field generator coils 2304-1, 2304-2, and 2304-3 electrically connected to a power supply 2318. An EM system controller 2308 may be in operable communication with a plurality of switches K1, K2, and K3 and a position sensor 2316. The plurality of switches K1, K2, and K3 may be located in a switch module (e.g., switch module 2010 of FIG. 20). The EM system controller 2308 may be configured to selectively activate one or more subsets of field generator coils 2304, either simultaneously, sequentially, or in a round-robin configuration, based on a position and/or movement of the position sensor 2316 within and/or between adjacent control volumes (e.g., control volumes 2112 of FIG. 21).

The EM system controller 2308 may be configured to control one or more switches to selectively activate one or more subsets of field generator coils 2304. For example, the EM system controller 2308 may selectively activate the first subset of field generator coils 2304-1 by closing the switch K1. Similarly, the EM system controller 2308 may selectively activate the second subset of field generator coils 2304-2 by closing the switch K2. Likewise, the EM system controller 2308 may selectively activate the third subset of field generator coils 104-3 by closing the switch K3. In some embodiments, the EM system controller 2308 may simultaneously activate two or more subsets of field generator coils 2304. For example, the EM system controller 2308 may simultaneously activate the first and second subsets of field generator coils 2304-1 and 2304-2 by closing the switches K1 and K2. Similarly, the EM system controller 2308 may simultaneously activate the first and third subsets of field generator coils 2304-1 and 2304-3 by closing the switches K1 and K3. Likewise, the EM system controller 2308 may simultaneously activate the second and third subsets of field generator coils 2304-2 and 2304-3 by closing the switches K2 and K3. Optionally, the EM system controller 2308 may simultaneously activate the first, second, and third subsets of field generator coils 2304-1, 2304-2, and/or 2304-3 by simultaneously closing the switches K1, K2, and/or K3, respectively. In some embodiments, the EM system controller 2308 may sequentially close the switches K1, K2, and/or K3. In some other embodiments, the EM system controller 2308 may close the switches K1, K2, and/or K3 in alternating manner. In some embodiments, the EM system controller 2308 may close the switches K1, K2, and/or K3 at a same frequency or at different frequencies. In some embodiments, the EM system controller 2308 may close/open the switches K1, K2, and/or K3 for different lengths of time, so as to activate or power off the subsets of field generator coils 2304 for different lengths of time.

5. Layout of Field Generator Coils and Working Volumes

Figure 24:
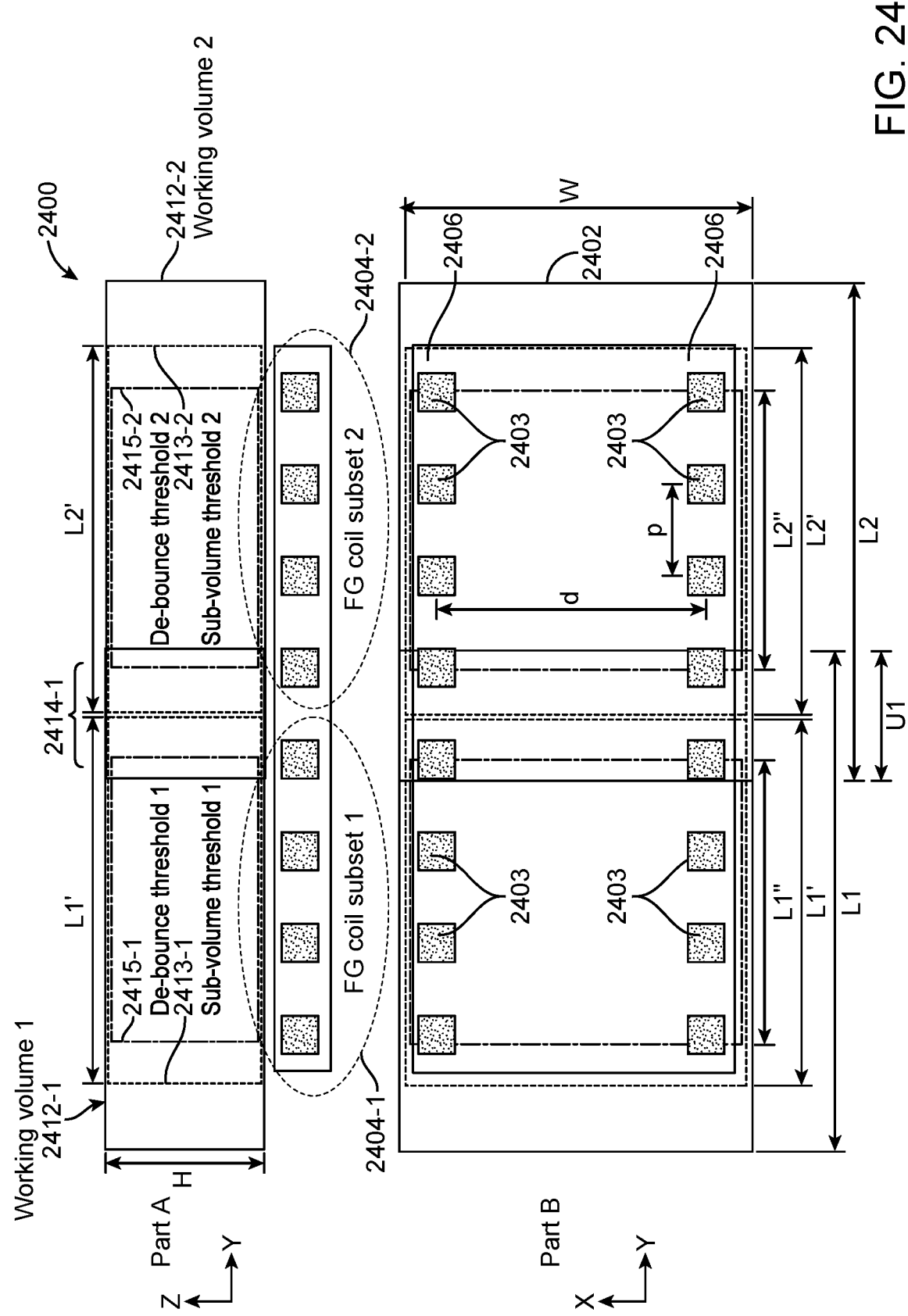
FIG. 24 illustrates schematic layouts of field generator coils and working volumes within an EM tracking surgical system, in accordance with some embodiments.

FIG. 24 illustrates schematic layouts of field generator coils and working volumes within an EM tracking surgical system, in accordance with some embodiments. Part A of FIG. 24 illustrates a schematic side view of a portion of an EM tracking surgical system 2400, and Part B of FIG. 24 illustrates a schematic top view of the portion of the system 2400.

As shown in FIG. 24, a first subset of field generator coils 2404-1 and a second subset of field generator coils 2404-2 may be embedded along a length portion of a surgical bed 2402. A first working volume 2412-1 may be defined above the first subset of field generator coils 2404-1, and a second working volume 2412-2 may be defined above the second subset of field generator coils 2404-2. The dimensions of the first working volume 2412-1 may be given by a length L1, a width W, and a height H. The dimensions of the second working volume 2412-2 may be given by a length L2, a width W, and a height H. In some embodiments, the lengths L1 and L2 may be substantially the same. In other embodiments, the lengths L1 and L2 may be different. For example, in some instances, the length L1 may be less than the length L2. In other instances, the length L1 may be greater than the length L2. In some alternative embodiments (not shown), the widths of the first and second working volumes 2412 may be different. Optionally, the heights of the first and second working volumes 2412 may be different.

Each working volume 2412 may comprise a sub-volume threshold located within each working volume. The sub-volume threshold is located at a boundary between overlapping working volumes. The sub-volume threshold may correspond to a transition zone as the sensor moves between overlapping working volumes. For example, the first working volume 2412-1 may comprise a first sub-volume threshold 2413-1, and the second working volume 2412-2 may comprise a second sub-volume threshold 2413-2. The first sub-volume threshold 2413-1 may have a length L1', and the second sub-volume threshold 2413-2 may have a length L2'. In some embodiments, the lengths L1' and L2' may be substantially the same. In other embodiments, the lengths L1' and L2' may be different. The widths of the first and second sub-volume thresholds may be the same, and the heights of the first and second sub-volume thresholds may be the same. In some alternative embodiments (not shown), the widths of the first and second sub-volume thresholds may be different. Optionally, the heights of the first and second sub-volume thresholds may be different.

Each working volume 2412 may further comprise a de-bounce threshold located within each sub-volume threshold. For example, the first working volume 2412-1 may comprise a first de-bounce threshold 2415-1, and the second working volume 2412-2 may comprise a second de-bounce threshold 2415-2. The second working volume may be activated once the sensor leaves the first de-bounce threshold and enters the second de-bounce threshold. Similarly, the first working volume may be activated once the sensor leaves the second de-bounce threshold and enters the first de-bounce threshold. Accordingly, the de-bounce thresholds may serve as "de-bouncing switches" for determining which working volume is to be activated. The first de-bounce threshold 2415-1 may have a length L1", and the second de-bounce threshold 2415-2 may have a length L2". In some embodiments, the lengths L1" and L2" may be substantially the same. In other embodiments, the lengths L1" and L2" may be different. The widths of the first and second de-bounce thresholds may be the same, and the heights of the first and second de-bounce thresholds may be the same. In some alternative embodiments (not shown), the widths of the first and second de-bounce thresholds may be different. Optionally, the heights of the first and second de-bounce thresholds may be different.

As shown in FIG. 24, the first and second working volumes may overlap so as to form a first overlapping working volume 2414-1 disposed at a boundary between the first and second subsets of field generator coils 2404-1 and 2404-2. The first and second working volumes 2412-1 and 2412-2 may overlap by various amounts. For example, the first and second working volumes 2412-1 and 2412-2 may overlap by 1%, 2%, 5%, 10%, 15%, 20%, 25%, 30%, or more than 30%. The first and second working volumes 2412-1 and 2412-2 may be configured to overlap such that a position sensor can be accurately tracked and controlled near the boundaries of the control volumes 2412, and as a position sensor moves between adjacent working volumes 2412. The first overlapping working volume 2414-1 may have a length U1, a width W, and a height H.

Each subset of field generator coils 2404 may comprise a number of field generator coils 2403. The number of field generator coils 2403 in the subsets may be same or different. As shown in part B of FIG. 24, each subset of field generator coils 2404 may comprise eight field generator coils 2403. The field generator coils 2403 may be disposed along the edges of the surgical bed 2402 in two parallel rows 2406. The field generator coils 2403 may be spaced apart from one another along each row 2406, at a pitch p in the Y-direction. Laterally opposite field generator coils 2403 in the two rows 2406 may be spaced apart by a distance d from each other in the X-direction. The field generator coils 2403 in the subsets 2404 may be spaced in a configuration that allows an EM field of a predetermined strength to substantially extend over each working volume 2412.

6. Selective Activation of Field Generator Coils with One Position Sensor

Figure 25:
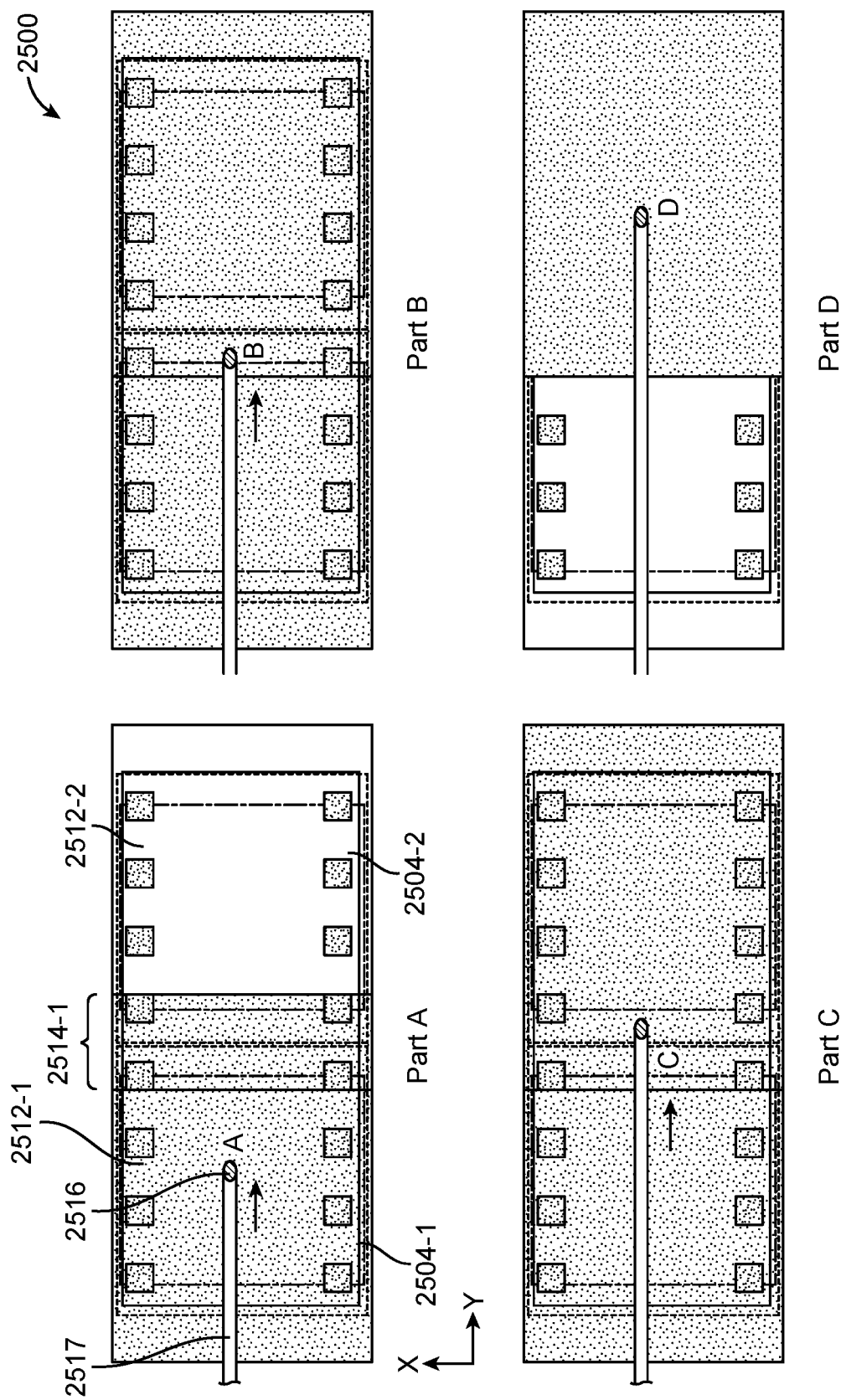
FIG. 25 illustrates selective activation of field generator coils and working volumes as a surgical tool comprising a position sensor moves within an EM tracking surgical system, in accordance with some embodiments.

FIG. 25 illustrates the selective activation of field generator coils and working volumes as a surgical tool comprising a position sensor moves within an EM tracking surgical system, in accordance with some embodiments. Parts A, B, C, and D of FIG. 25 illustrate schematic top views of a portion of an EM tracking surgical system 2500.

As shown in part A of FIG. 25, a position sensor 2516 may be disposed at a distal end of a surgical tool 2517. The surgical tools may include endoscopes, catheters, ureteroscopes, or other similar devices. Initially, the surgical tool 2517 may be positioned such that the position sensor 2516 is located at position A. Position A may be a point within a first working volume 2512-1 above a first subset of field generator coils 2504-1. An EM system controller (e.g., EM system controller 2508) may detect that the position sensor 2516 is within the first working volume 2512-1 and not in the second working volume 2512-2. Additionally, the EM system controller may detect that the position sensor 2516 is within the first working volume 2512-1 but outside of a first overlapping working volume 2514-1. The first overlapping working volume 2514-1 may be an overlapping region between the first and second working volumes 2512-1 and 2512-2. Accordingly, the EM system controller may selectively activate the first subset of field generator coils 2504-1 without activating the second subset of field generator coils 2504-2. When the first subset of field generator coils 2504-1 is activated, the first working volume 2512-1 may become an active working volume, as indicated by the shaded region over the first working volume 2512-1.

During a surgical procedure, the surgical tool 2517 may move to a different location, such that the position sensor 2516 may move to position B shown in part B of FIG. 25. Position B may be a point that lies within the first working volume 2512-1 and the first overlapping working volume 2514-1. Since position B lies near the boundary of the first working volume 2512-1, the EM system controller may activate the second subset of field generator coils 2504-2 in addition to the first subset of field generator coils 2504-1, to ensure that the position sensor 2516 can be accurately tracked near the boundary between adjacent working volumes 2512. When the first and second subset of field generator coils 2504-1 and 2504-2 are activated, the first and second working volumes 2512-1 and 2512-2 become active working volumes, as indicated by the shaded regions over the first and second working volumes 2512-1 and 2512-2.

Next, the surgical tool 2517 may move to a different location, such that the position sensor 2516 may move to position C shown in part C of FIG. 25. Position C may be another point in the first overlapping working volume 2514-1. However, unlike position B, position C may lie within the second working volume 2512-2. Since position C lies near the boundary of the second working volume 2512-2, the EM system controller may continue to activate both the first and second subsets 2512, to ensure that the position sensor 2516 can be accurately tracked near the boundary between adjacent working volumes 2512.

Next, the surgical tool 2517 may move to a different location, such that the position sensor 2516 may move to position D shown in part D of FIG. 25. The EM system controller may detect that the position sensor 2516 is within the second working volume 2512-2 but outside of the first overlapping working volume 2514-1. Accordingly, the EM system controller may continue to activate the second subset of field generator coils 2504-2, but power off the first subset of field generator coils 2504-1.

Figure 26:
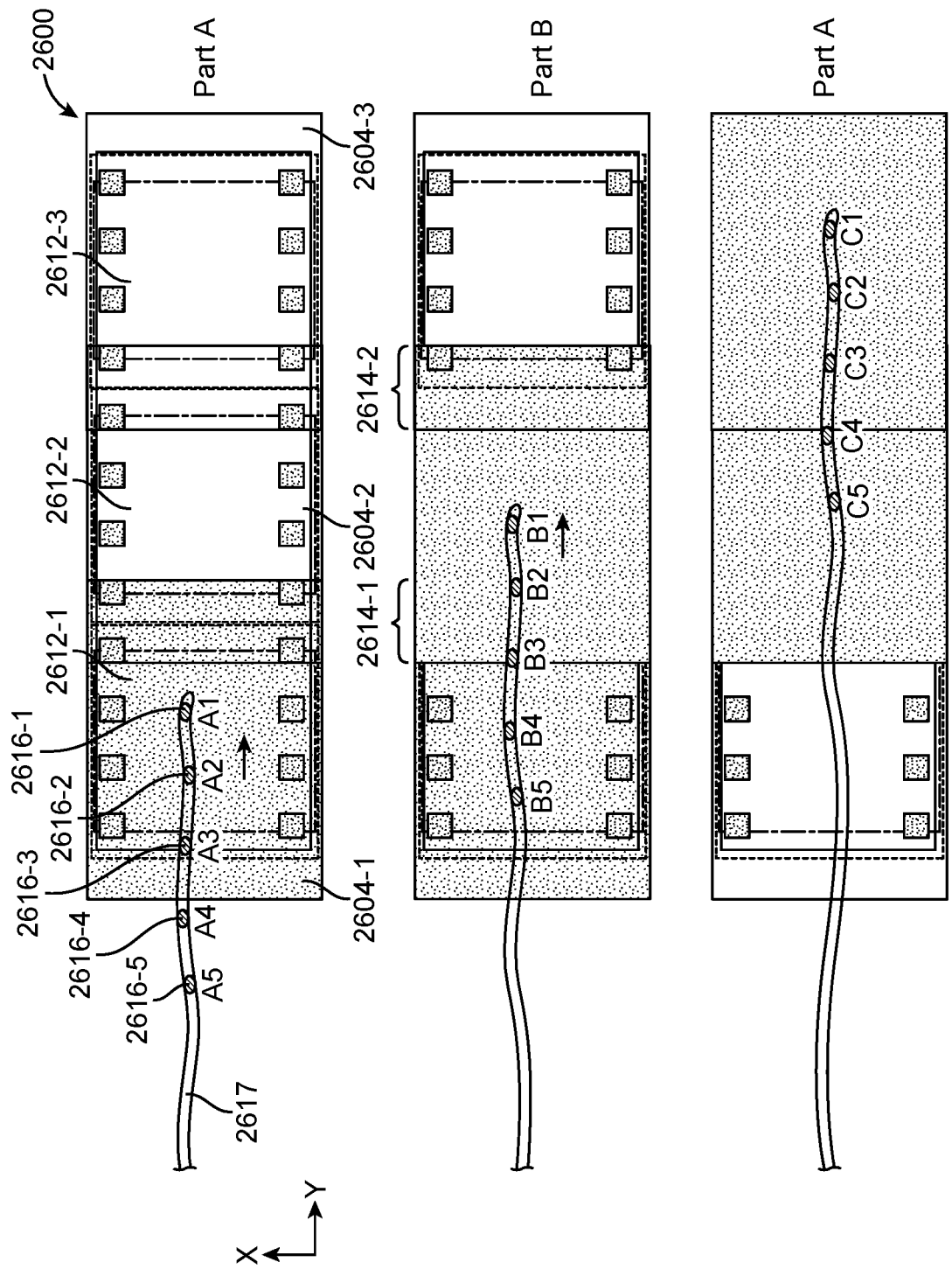
FIG. 26 illustrates selective activation of field generator coils and working volumes as a surgical tool comprising a plurality of position sensors moves within an EM tracking surgical system, in accordance with some embodiments.

7. Selective Activation of Field Generator Coils with a Plurality of Position Sensors FIG. 26 illustrates selective activation of field generator coils and working volumes as a surgical tool comprising a plurality of position sensors moves within an EM tracking surgical system, in accordance with some embodiments. Parts A, B, and C of FIG. 26 illustrate schematic top views of a portion of an EM tracking surgical system 2600. The embodiment of FIG. 26 has similarities to the embodiment of FIG. 25.

In FIG. 26, a surgical tool 2617 may be a flexible probe or shaft capable of twisting and bending about different directions. Additionally, the surgical tool 2617 may comprise a plurality of position sensors 2616 that include position sensors 2616-1, 2616-2, 2616-3, 2616-4, and 2616-5. For example, a position sensor 2616-1 may be disposed at a distal end of the surgical tool 2617, and a plurality of position sensors 2616-2, 2616-3, 2616-4, and 2616-5 may be spaced apart along a length of the surgical tool 2617. By placing the plurality of position sensors 2616 at different locations along the surgical tool 2617, the position/orientation/shape of the surgical tool 2617 can be determined through use of an EM field, which may be important during a surgical procedure as the tool 2617 is being inserted into a patient's body. In some cases, the position/orientation/shape of the surgical tool 2617 that is obtained by an EM system controller can be mapped onto the fluoroscopic image of the patient's body in real-time as the surgical procedure is being performed.

Additionally, in FIG. 26, more than two working volumes may be provided. For example, the EM tracking surgical system 2600 may comprise three working volumes 2612: a first working volume 2612-1, a second working volume 2612-2, and a third working volume 2612-3. In examples, 4, 5, 6, 7, 8, 9, 10, or more than 10 working volumes 2612 may be provided.

As shown in part A of FIG. 26, the position sensors 2616-1, 2616-2, 2616-3, 2616-4, and 2616-5 may be located at positions A1, A2, A3, A4, and A5, respectively. Positions A1, A2, and A3 may lie within the first working volume 2612-1 above a first subset of field generator coils 2604-1. Positions A4 and A5 may lie outside of the first working volume 2612-1 and/or any working volume. An EM system controller (e.g., EM system controller 2008 of FIG. 20) may detect that the position sensors 2616-1, 2616-2, and 2616-3 are within the first working volume 2612-1, and not in the second and third working volumes 2612-2 and 2612-3. Additionally, the EM system controller may detect that the position sensors 2616-1, 2616-2, and 2616-3 are within the first working volume 2612-1 outside of a first overlapping working volume 2614-1. Accordingly, the EM system controller may selectively activate the first subset of field generator coils 2604-1 without activating the second subset of field generator coils 2604-2.

During a surgical procedure, the surgical tool 2617 may move from the position shown in part A to the position shown in part B of FIG. 26. Referring to part B of FIG. 26, the position sensors 2616-1, 2616-2, 2616-3, 2616-4, and 2616-5 may be located at positions B1, B2, B3, B4, and B5, respectively. Position B1 may be a point that lies within the second working volume 2612-2 outside of the first overlapping working volume 2614-1. Position B2 may be a point that lies within the second working volume 2612-2 and the first overlapping working volume 2614-1. Position B3 may be a point that lies within the first working volume 2612-1 and the first overlapping working volume 2614-1. Positions B4 and B5 may be different points that lie within the first working volume 2612-1 outside of the first overlapping working volume 2614-1. Accordingly, the EM system controller may activate the second subset of field generator coils 2604-2 in addition to the first subset of field generator coils 2604-1, to ensure that the position sensor 2616 can be accurately tracked within the first and the second working volumes 2612-1 and 2612-2.

Next, the surgical tool 2617 may move from the position shown in part B to the position shown in part C of FIG. 26. Referring to part C of FIG. 26, the position sensors 2616-1, 2616-2, 2616-3, 2616-4, and 2616-5 may be located at positions C1, C2, C3, C4, and C5, respectively. Positions C1 and C2 may be different points that lie within the third working volume 2612-3 outside of a second overlapping working volume 2614-2. Position C3 may be a point that lies within the third working volume 2612-3 and the second overlapping working volume 2614-2. Positions C4 and C5 may be different points that lie within the second working volume 2612-2 outside of the second overlapping working volume 2614-2. None of the positions C1-C5 lies within the first working volume 2612-1 and/or the first overlapping working volume 2614-1. Accordingly, the EM system controller may activate the third subset of field generator coils 2604-3 in addition to the second subset of field generator coils 2604-2, to ensure that the position sensor 2616 can be accurately tracked within the second and the third working volumes. Additionally, the EM system controller may power off the first subset of field generator coils 2604-1 since none of the position sensors 2616 lies within the first working volume 2612-1.

Figure 27:
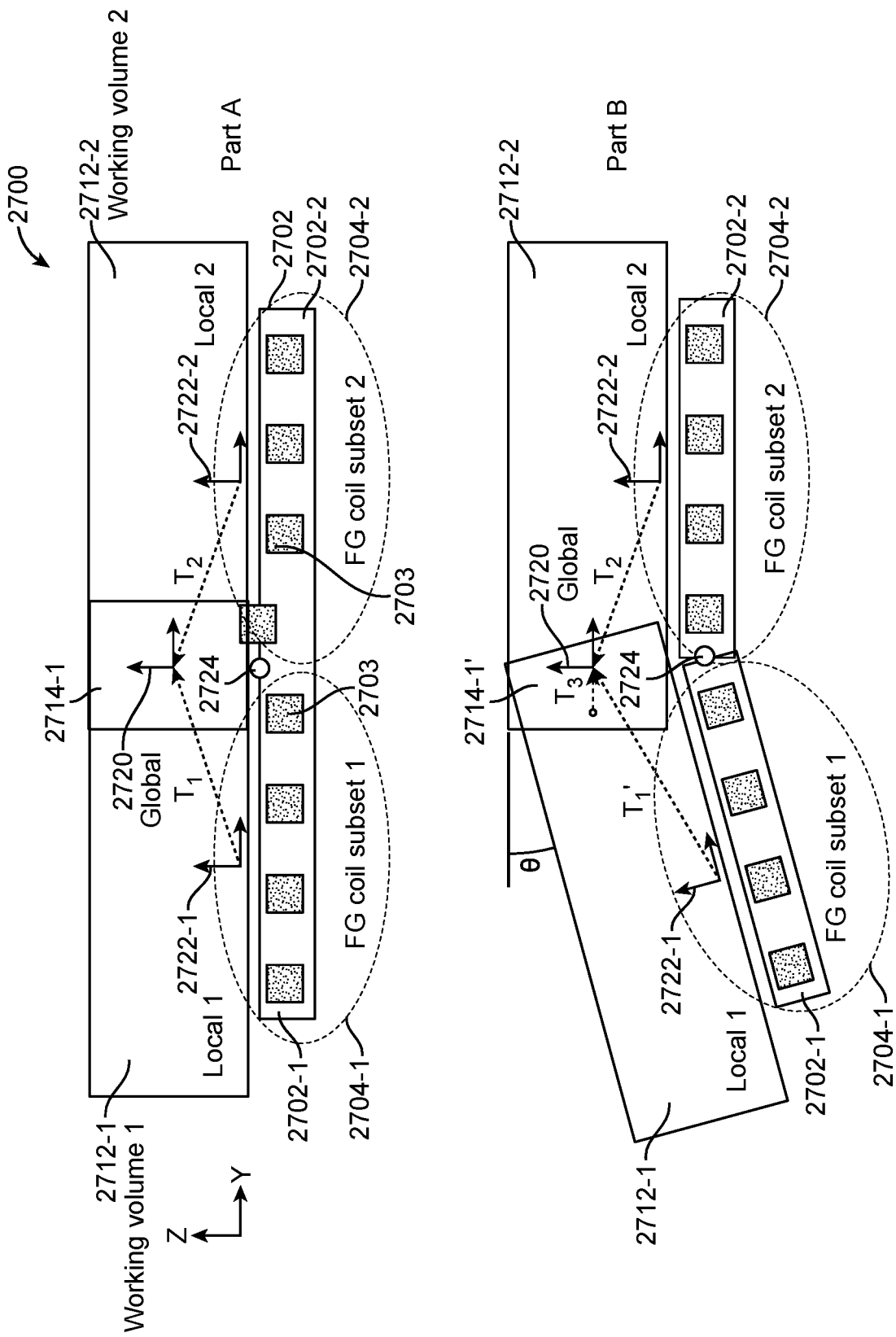
FIG. 27 illustrates schematic views of an EM tracking surgical system having reconfigurable bed portions, in accordance with some embodiments.

Although FIG. 27 illustrates the tracking of a surgical tool having a plurality of position sensors, one of ordinary skill in the art would appreciate that the EM system can also be used to track a plurality of surgical tools having a plurality of position sensors. Each surgical tool may have one or multiple position sensors.

8. EM Tracking Surgical Systems Having Reconfigurable Bed Portions

FIG. 27 illustrates schematic views of an EM tracking surgical system having reconfigurable bed portions, in accordance with some embodiments. Part A of FIG. 27 illustrates a side view of a portion of a floating EM field generator system 2700 when a surgical bed is in a first position. Part B of FIG. 27 illustrates the side view of the system 2700 when the surgical bed is in a second position.

As shown in FIG. 27, a surgical bed 2702 may comprise reconfigurable bed portions that can move relative to each other. For example, the surgical bed 2702 may comprise a first bed portion 2702-1 and a second bed portion 2702-2 connected at a hinge 2724 that allows the bed portions to move (e.g., rotate and/or slide) relative to each other. A first subset of field generator coils 2704-1 may be embedded along a length of a first arm portion 2702-1. A second subset of field generator coils 2704-2 may be embedded along a length of the second arm portion 2702-2. Accordingly, the first and second subsets of field generator coils 2704 may be embedded along a length of arm portions that are adjacent to the surgical bed 2702.

A first working volume 2712-1 may be defined above the first subset of field generator coils 2704-1, and a second working volume 2712-2 may be defined above the second subset of field generator coils 2704-2, similar to the embodiment previously described in FIG. 24. In some embodiments, the dimensions and/or size of the first and second working volumes 2712-1 and 2712-2 may be the same. Alternatively, the dimensions and/or size of the first and second working volumes 2712-1 and 2712-2 may be different.

As shown in FIG. 27, the first and second working volumes may overlap so as to form a first overlapping working volume 2714-1 disposed at a boundary between the first and second subsets of field generator coils 2704-1 and 2704-2. The first and second working volumes 2712-1 and 2712-2 may be configured to overlap by various amounts. For example, the first and second working volumes 2712-1 and 2712-2 may be configured to overlap by 1%, 2%, 5%, 10%, 15%, 20%, 25%, 30%, or more than 30%. The first and second working volumes 2712-1 and 2712-2 may be configured to overlap such that one or more position sensors, such as position sensors 2716 discussed above, can be accurately tracked and controlled near the boundaries of the control volumes 2712, and as the position sensor(s) 2716 moves between adjacent working volumes 2712.

Each subset of field generator coils 2704 may comprise a number of field generator coils 2703. The number of field generator coils 2703 in the subsets 2704 may be same or different. In FIG. 27, each subset of field generator coils 2704 may comprise eight field generator coils 2703, for example similar to the embodiment previously described in FIG. 24. The field generator coils 2703 may be disposed along the edges of the surgical bed 2702 in two parallel rows (not shown in FIG. 27). The field generator coils 2703 may be spaced apart from one another along each row (e.g., at a pitch p in the Y-direction). Laterally opposite field generator coils 2703 in the two rows may be spaced apart (e.g., by a distance d) from each other in the X-direction. The field generator coils 2703 in the subsets 2704 may be spaced in a configuration that allows an EM field of a predetermined strength to substantially extend over each working volume 2712.

As shown in FIG. 27, a global coordinate system 2720 may be defined above a center portion of the surgical bed 2702. For example, the global coordinate system 2720 may be defined above a boundary line between the first bed portion 2702-1 and the second bed portion 2702-2. An origin of the global coordinate system 2720 may lie above the center portion of the surgical bed 2702 along the Z-direction. The origin of the global coordinate system 2720 may also lie at a predetermined location above the hinge 2724 when the surgical bed is in the position shown in part A of FIG. 27. The origin of the global coordinate system 2720 may serve as a datum point from which the positions of a patient's body, the subsets of field generator coils 2704, and the working volume 2712 may be defined.

A first local coordinate system 2722-1 may be defined above a center portion of the first bed portion 2702-1. Likewise, a second local coordinate system 2722-2 may be defined above a center portion of the second bed portion 2702-2. The first local coordinate system 2722-1 may or may not have an origin that lies at a center portion of the first working volume 2712-1. Similarly, the second local coordinate system 2722-2 may or may not have an origin that lies at a center portion of the second working volume 2712-2. For example, as shown in part A of FIG. 27, the origin of the first local coordinate system 2722-1 may lie below the center portion of the first working volume 2712-1, and in close proximity to the first bed portion 2702-1. Likewise, the origin of the second local coordinate system 2722-2 may lie below the center portion of the second working volume 2712-2, and in close proximity to the second bed portion 2702-2.

Vectors may be defined between the global coordinate system 2720 and the local coordinate systems 2722-1 and 2722-2. For example, a vector T1 may be defined from the origin of the first local coordinate system 2722-1 to the origin to the global coordinate system 2720. A vector T2 may be defined from the origin of the second local coordinate system 2722-2 to the origin to the global coordinate system 2720. In some embodiments, another vector (not shown) may be defined from the origin of the first local coordinate system 2722-1 to the origin of the second local coordinate system 2722-2. The vectors T1 and T2 may be used to define the spatial relationship between the first working volume 2712-1 and the second working volume 2712-2. In particular, the vectors T1 and T2 may be used to define the spatial relationship between the first and second working volumes 2712-1 and 2712-2 relative to the datum point (origin of the global coordinate system 2720) as the first and second bed portions 2702-1 and 2702-2 move relative to each other.

As shown in part A of FIG. 27, the first bed portion 2702-1 and the second bed portion 2702-2 may initially lie on a same horizontal plane extending along the Y-axis direction. The first and second bed portions 2702-1 and 2702-2 may be configured to move relative to each other. For example, as shown in part B of FIG. 27, the first bed portion 2702-1 may rotate by an angle θ in a clockwise direction about an X-axis extending through the hinge 2724. The first bed portion 2702-1 may be rotated, for example, to lower or raise a portion of a patient's body that is supported by the first bed portion 2702-1. Since the first control volume 2712-1 is defined by the EM field generated by the first subset of field generator coils 2704-1, the first control volume 2712-1 may also rotate by the angle θ in a clockwise direction about the X-axis. As shown in part B of FIG. 27, it may be observed that the origin of the first local coordinates system 2722-1 has shifted to a new location. Accordingly, a new vector T1' may be defined from the shifted origin of the first local coordinates system 2722-1 to the origin of the global coordinates system 2720, whereby the vector T1' is different from the vector T1. Since the second bed portion 2702-2 is not rotated relative to the global coordinates system 2720, the origin of the second local coordinates system 2722-2 remains unchanged, and therefore the vector T2 remains the same. The vectors T1' and T2 may be used to define the spatial relationship between the first and second working volumes 2712-1 and 2712-2 relative to the datum point (origin of the global coordinate system 2720) after the first bed portion 2702-1 has moved relative to the second bed portion 2702-2.

Although part B of FIG. 27 illustrates movement of the first bed portion 2702-1 relative to the second bed portion 2702-2, the movement between the bed portions is not limited thereto. For example, in some embodiments, the second bed portion 2702-2 may move relative to the first bed portion 2702-1. Optionally, the first and second bed portions 2702-1 and 2702-2 may simultaneously move relative to each other such that the origins of the first and second local coordinate systems shift to different locations. The relative movement between the bed portions 2702-1 and 2702-2 may comprise a rotational motion, a translational motion, and/or a combination of rotational and translational motion, about one or more axes. Accordingly, relative movement of the bed portions 2702-1 and 2702-2 in one or more degrees of freedom (e.g., six degrees of freedom) may be contemplated.

In some embodiments, a position, shape, and/or size of the overlapping working volume 2714 between adjacent working volumes may change when the bed portions move relative to each other. For example, as shown in part A of FIG. 27, a center (or centroid) of the first overlapping working volume 2714-1 may be located at the origin of the global coordinates system 2720. The first overlapping working volume 2714-1 may have a regular shape (e.g., defined by a length U1, width W, and height H, similar to the embodiment previously shown in FIG. 24).

When the first bed portion 2702-1 rotates relative to the second bed portion 2702-2, the position, shape, and/or size of the first overlapping working volume 2714-1 may change. For example, as shown in part B of FIG. 27, the first overlapping working volume 2714-1 may transform to overlapping working volume 2714-1' having an irregular shape (e.g., having a trapezoidal-like profile as viewed from a side of the overlapping working volume 2714-1'). The origin of the global coordinates system 2720 remains unchanged by the relative rotation of the bed portions. Unlike part A of FIG. 27, the center (or centroid) of the overlapping working volume 2714-1' is not located at the origin of the global coordinates system 2720 after the rotation. Instead, the center (or centroid) of the overlapping working volume 2714-1' may be offset from the origin of the global coordinates system 2720 by a vector T3 after the rotation.

Figure 28A:
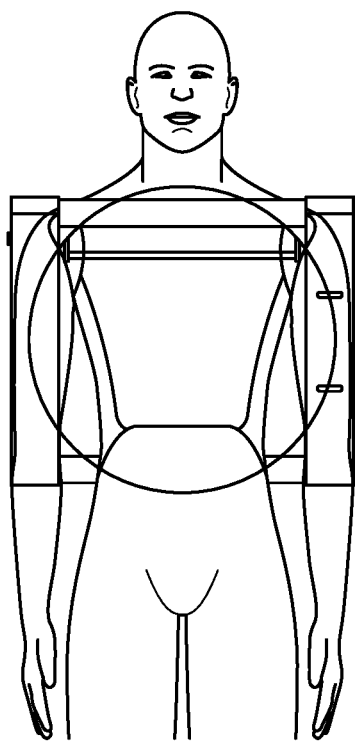
FIGS. 28A and 28B illustrate sizing of a reconfigurable bed portion of an EM tracking surgical system based on exemplary dimensions of a human torso, in accordance with some embodiments.
Figure 28B:
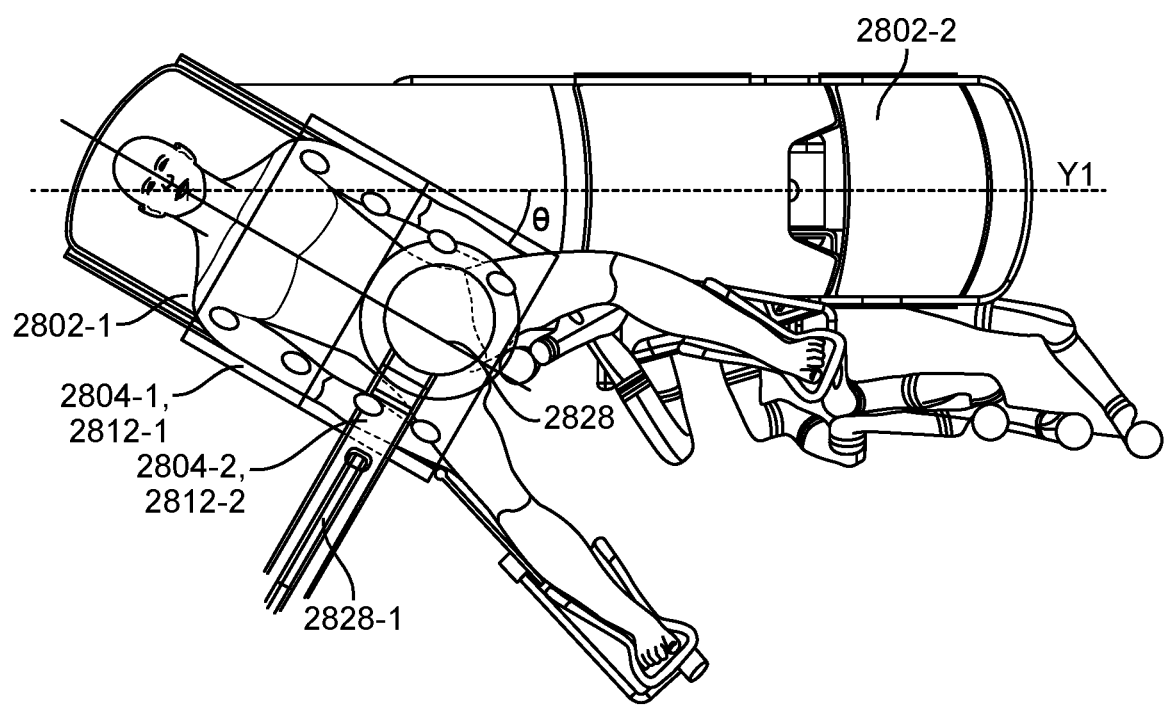

FIGS. 28A and 28B illustrate sizing of a reconfigurable bed portion of an EM tracking surgical system based on exemplary dimensions of a human torso, in accordance with some embodiments. FIG. 28A illustrates exemplary dimensions of a human torso and a working volume that is defined based on those exemplary dimensions. FIG. 28B illustrates a schematic view of a patient who is placed on a reconfigurable bed portion of an EM tracking surgical system.

FIG. 28A illustrates exemplary dimensions of a human torso. For example, a length of a longest human torso (as measured from neck to anus) may be about 32.9 inches, and a width of the human torso may be about 13 inches. A working volume of each subset of field generator coils may be defined based on those dimensions.

As shown in FIG. 28B, the first bed portion 2802-1 may be rotated relative to the second bed portion 2802-2, such that the patient's body is rotated an angle θ relative to a longitudinal axis Y1 extending longitudinally along the second bed portion 2802-2.

A first working volume 2812-1 and a second working volume 2812-2 may be associated with the first subset of field generator coils 2804-1 and the second subset of field generator coils 2804-2, respectively. In some embodiments, the first working volume 2812-1 may be a cylinder. The diameter of the cylinder may be about 5", 6", 7", 8", 9", 10", 11", 12", 13", 14", 15", 16" 17", 18", 19", 20", 21", 22", 23", 24", 25", or greater than 25". The height of the cylinder may be about 5", 6", 7", 8", 9", 10", 11", 12", 13", 14", 15", 16" 17", 18", 19", 20", 21", 22", 23", 24", 25", or greater than 25". In some examples, a cylinder may have a minimum diameter and height of about 5"×5". In other examples, a cylinder may have a maximum distance and height of about 25"×25". Optionally, in some examples, each of the diameter and height of a cylinder may be less than 5", or greater than 25". Optionally, the first working volume 2812-1 may be a cuboid. The length of the cuboid may be about 5", 6", 7", 8", 9", 10", 11", 12", 13", 14", 15", 16" 17", 18", 19", 20", 21", 22", 23", 24", 25", or greater than 25". The width of the cuboid may be about 5", 6", 7", 8", 9", 10", 11", 12", 13", 14", 15", 16" 17", 18", 19", 20", 21", 22", 23", 24", 25", or greater than 25". The height of the cuboid may be about 5", 6", 7", 8", 9", 10", 11", 12", 13", 14", 15", 16" 17", 18", 19", 20", 21", 22", 23", 24", 25" or greater than 25". In some examples, a cuboid may have a minimum length, width, and height of about 5"×5"×5". In other examples, a cuboid may have a maximum length, width, and height of about 25"×25"×25". Optionally, in some examples, each of the length, width, and height of a cuboid may be less than 5", or greater than 25". The second working volume 2812-2 may or may not have the same shape and/or dimensions as the first working volume 2812-1. Any shape and/or dimensions for the first and second working volumes may be contemplated.

As shown in FIG. 28B, a fluoroscopic imaging system 2828 may be placed above the patient's body. For example, the fluoroscopic imaging system 2828 may be placed within or above the second working volume 2812-2. The fluoroscopic imaging system 2828 may be supported by a mechanical arm 2828-1 extending towards and/or over the first bed portion 2802-1. In the example of FIG. 28B, the fluoroscopic imaging system 2828 may be used to capture fluoroscopic images of the patient's body within the second working volume 2812-2. Since the second subset of field generator coils 2804-2 is placed within arms that are adjacent to the second bed portion 2802-2, a central portion of the surgical bed may be free enough of effects from the field generates such that fluoroscopy can be used with little or no obstruction.

Figure 29:
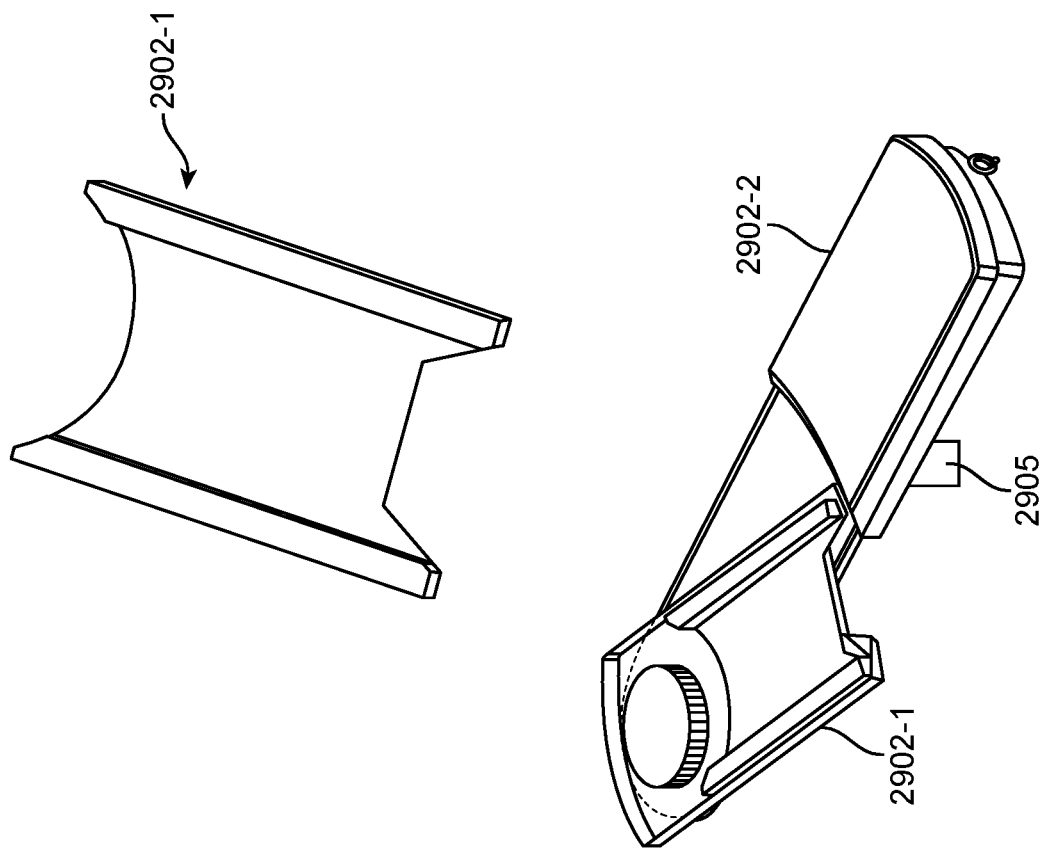
FIG. 29 illustrates a reconfigurable bed portion of an EM tracking surgical system, in accordance with some embodiments.
Figure 29:
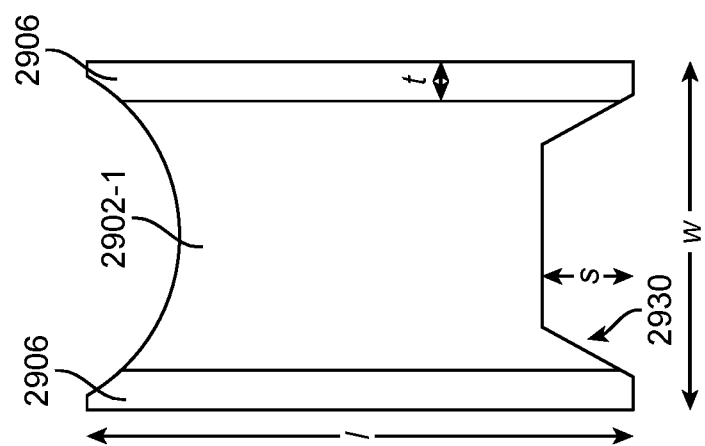

FIG. 29 illustrates a reconfigurable bed portion of an EM tracking surgical system, in accordance with some embodiments. As previously described in FIGS. 28A, and 28B, a surgical bed 2902 may comprise a first bed portion 2902-1 and a second bed portion 2902-2 that may be disposed on a base 2905. The first bed portion 2902-1 may be operably connected to a hinge 2924 that allows the first bed portion 2902-1 to move (e.g., rotate and/or translate) relative to the second bed portion 2902-2.

As shown in FIG. 29, a first bed portion 2902-1 may have a length l and a width w. In some embodiments, the length l may be about 29.5 inches, and the width w may be about 18.5 inches. In some embodiments, a cutout 2930 may be formed at an end of first bed portion 2902-1, so as to prevent mechanical interference as the first bed portion 2902-1 moves relative to the second bed portion 2902-2. In the example of FIG. 29, the cutout 2930 may have a trapezoidal shape, and may be offset by a distance s from an edge portion of the first bed portion 2902-1.

The first bed portion 2902-1 may further include two arms 2906 that are adjacent to the surgical bed. As previously described, by placing a plurality of field generator coils within arms 2906 adjacent to the surgical bed 2902 (e.g., the first bed portion 2902-1), unobstructed use of fluoroscopy can be achieved to image at least a portion of a patient's body. Each row 2906 may have a width of t that is associated with an area of fluoro obstruction. In some embodiments, the width t may be less than or equal to about 2 inches. It should be noted that rows 2906 constitute areas of fluoroscopy obstruction, since the field generator coils are radio-opaque.

Figure 30:
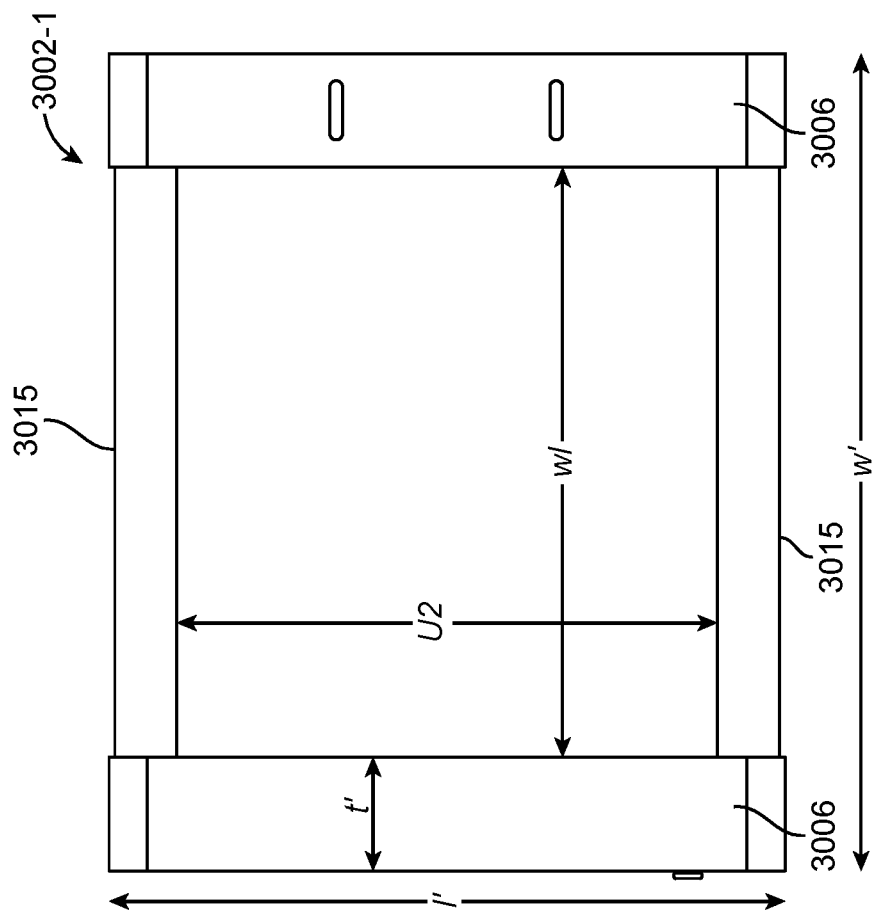
FIG. 30 illustrates dimensions and locations of field generator coils on a reconfigurable bed portion of an EM tracking surgical system, in accordance with some embodiments.

FIG. 30 illustrates the dimensions and locations of field generator coils on a reconfigurable bed portion of an EM tracking surgical system, in accordance with some embodiments. In the example of FIG. 30, a reconfigurable bed portion 3002-1 of a surgical bed may have a length l' and a width w'. In some embodiments, the length l' may be about 18.1 inches, and the width w' may be about 21.8 inches.

The bed portion 3002-1 may further include two parallel rows 3006 on its edges. In examples, the two parallel rows may comprise arms that are adjacent to the surgical bed. The arms may be decoupled from the surgical bed such that weight of a patient that bends a surgical bed may not adversely affect the placement of field generator coils within arms adjacent to the surgical bed. As previously described, by placing a plurality of field generator coils along two arms adjacent to the surgical bed, unobstructed use of fluoroscopy can be achieved to image at least a portion of a patient's body. Each row 3006 may have a width of t'. In some embodiments, the width t' may be less than or equal to about 3.025 inches. The two parallel rows 3006 may be separated by a distance w1. In some embodiments, the distance w1 may be about 15.75 inches. Additionally, rows 3006 may constitute areas of fluoroscopy obstruction, since the field generator coils are radio-opaque.

As shown in FIG. 30, end portions 3015 of the bed portion 3002-1 may correspond to regions where adjacent working volumes overlap. The end portions 114 may be separated by a distance U2. In some embodiments, the distance U2 may be about 14.5 inches.

Figure 31:
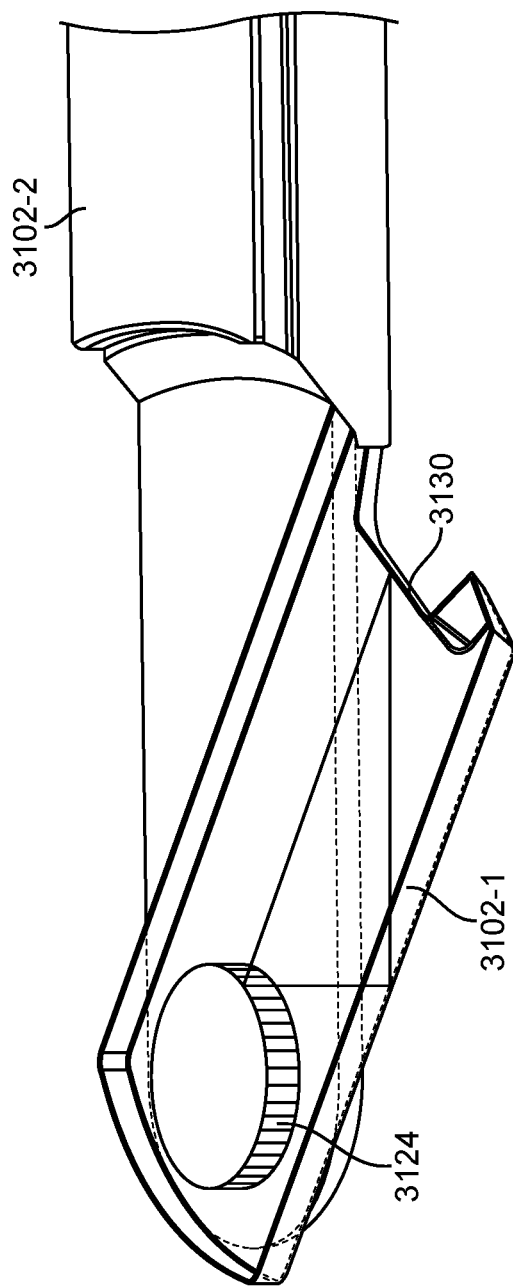
FIG. 31 illustrates an estimated length of a working volume based on the dimensions of a reconfigurable bed portion of an EM tracking surgical system, in accordance with some embodiments.

FIG. 31 illustrates an estimated length of a working volume based on the dimensions of a reconfigurable bed portion of an EM tracking surgical system, in accordance with some embodiments. As shown in FIG. 31, a distance from an edge of a hinge bearing 3124 to an edge of a cutout 3130 of a first bed portion 3102-1 may be denoted by l1. The distance l1 may be indicative of a length of a total working volume above the first bed portion 3102-1. In some embodiments, the distance l1 may be about 26.5 inches. FIG. 31 also illustrates first bed portion 3102-1 angled with respect to second bed portion 3102-2.

Figure 32:
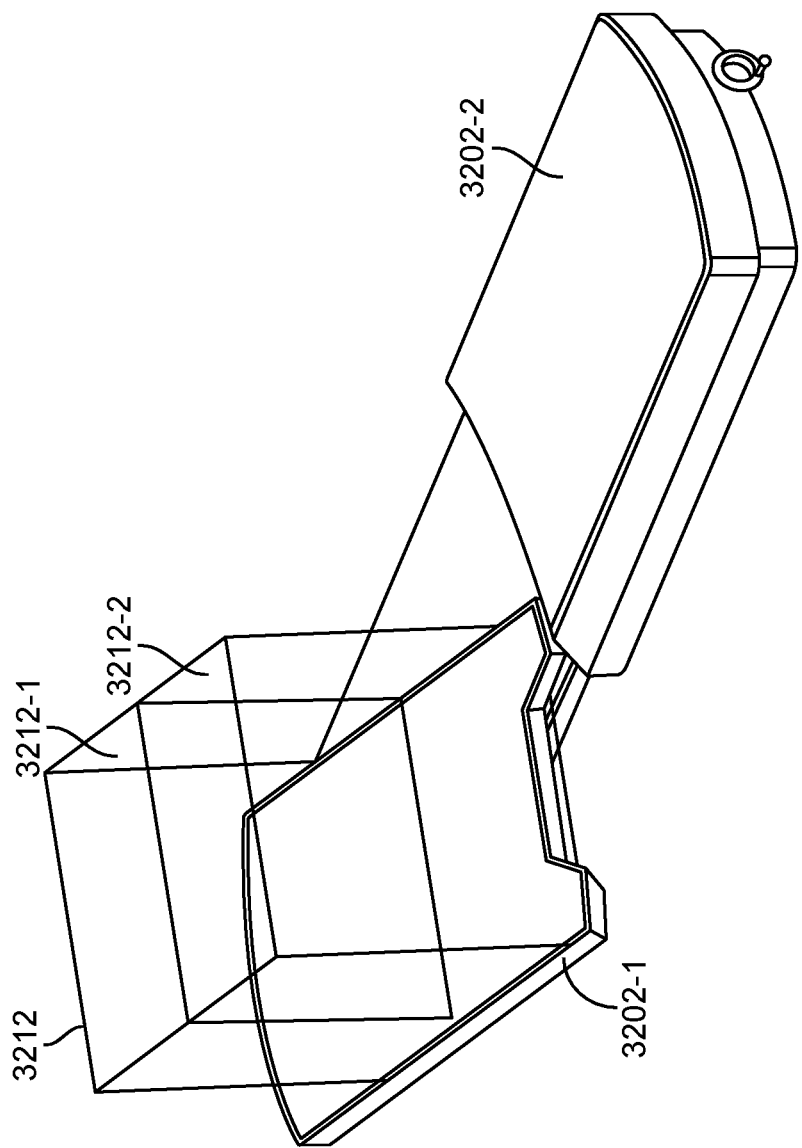
FIG. 32 illustrates an exemplary working volume above a reconfigurable bed portion of an EM tracking surgical system, in accordance with some embodiments.

FIG. 32 illustrates an exemplary working volume above a reconfigurable bed portion of an EM tracking surgical system, in accordance with some embodiments. As shown in FIG. 32, a total working volume 3212 may be defined above a first bed portion 3202-1 of a surgical bed 3202. In FIG. 32, first bed portion 3202-1 is shown angled with respect to second bed portion 3202-2. The total working volume 3212 may comprise a first working volume 3212-1 and a second working volume 3212-2. The total working volume 3212 may have a length LT, a width W, and a height H. In some embodiments, the length LT may be about 31 inches, the width W may be about 19 inches, and the height H may be about 19.7 inches. It should be noted that the invention is not limited thereto, and that any dimensions of the total working volume may be contemplated. As previously described, the first working volume 3212-1 and the second working volume 3212-2 may overlap, which can help to minimize deadzones (places where a position sensor cannot be tracked, either due to a weak EM field or EM interference).

As used herein A and/or B encompasses one or more of A or B, and combinations thereof such as A and B. It will be understood that although the terms "first," "second," "third" etc. may be used herein to describe various elements, components, regions and/or sections, these elements, components, regions and/or sections should not be limited by these terms. These terms are merely used to distinguish one element, component, region or section from another element, component, region or section. Thus, a first element, component, region or section discussed below could be termed a second element, component, region or section without departing from the teachings of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including," when used in this specification, specify the presence of stated features, regions, integers, steps, operations, elements and/or components, but do not preclude the presence or addition of one or more other features, regions, integers, steps, operations, elements, components and/or groups thereof.

Furthermore, relative terms, such as "lower" or "bottom" and "upper" or "top" may be used herein to describe one element's relationship to other elements as illustrated in the figures. It will be understood that relative terms are intended to encompass different orientations of the elements in addition to the orientation depicted in the figures. For example, if the element in one of the figures is turned over, elements described as being on the "lower" side of other elements would then be oriented on the "upper" side of the other elements. The exemplary term "lower" can, therefore, encompass both an orientation of "lower" and "upper," depending upon the particular orientation of the figure. Similarly, if the element in one of the figures were turned over, elements described as "below" or "beneath" other elements would then be oriented "above" the other elements. The exemplary terms "below" or "beneath" can, therefore, encompass both an orientation of above and below.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

What is claimed is:

1. A floating electromagnetic field generator system, comprising:
    a surgical bed platform including a first bed portion and a second bed portion, the first bed portion being movable relative to the second bed portion;
    a brace disposed within the surgical bed platform and connected to the surgical bed platform;
    a first arm attached to the brace and including a first arm portion connected to a second arm portion, the first arm portion having a first field generator coil connected thereto, the second arm portion having a second field generator coil connected thereto, the first arm portion configured to rotate relative to the second arm portion; and
    a second arm attached to the brace and having at least one field generator coil embedded therein, the second arm positioned on opposing side of the surgical bed platform from the first arm.

2. The system of claim 1, wherein the brace maintains relative position between the first arm and the second arm as the first arm is displaced.

3. The system of claim 1, wherein the first arm and the second arm are configured to stay rigid independent of bending or movement of the surgical bed platform due to a weight of a patient.

4. The system of claim 1, wherein the first arm is decoupled from the surgical bed platform so as to allow the bed to bend without placing direct pressure on the arm.

5. The system of claim 4, wherein the second arm is decoupled from the surgical bed platform as to allow the bed to bend without placing direct pressure on the arms.

6. The system of claim 1, wherein the first and second generator coils are configured to generate a magnetic field within a first control volume and a second control volume, respectively.

7. The system of claim 6, wherein first control volume is configured to rotate with respect to an X-axis extending through the connection between the first arm portion and second arm portion.

8. The system of claim 7, further comprising an intermediate brace has a width between three inches and five inches.

9. The system of claim 1, further comprising a base supporting the surgical bed platform, and a base connecting component comprising an intermediate brace.

10. A system, comprising:
a first surgical bed platform that is connected to, and movable with respect to, a second surgical bed platform, the first surgical bed platform and the second surgical bed platform configured to support a patient thereon, the first surgical bed platform configured to rotate relative to a longitudinal axis of the second surgical bed platform along a plane defined by the second surgical bed platform to move a position of the patient;
a brace connected to the first surgical bed platform;
a first arm that is attached to the brace, and having at least one field generator coil connected thereto, wherein the first arm includes a first portion a second portion, and a hinge connecting the first portion and the second portion, the first portion having a first field generator coil connected thereto, the second portion having a second field generator coil connected thereto, the first portion configured to rotate about the hinge relative to the second arm portion; and
a second arm attached to the brace, the second arm positioned on opposing side of the surgical bed platform from the first arm having the at least one field generator coil connected thereto.

11. The system of claim 10, wherein the brace maintains relative position between the first arm and the second arm as at least one of the first arm or the second arm is displaced.

12. The system of claim 10, wherein each of the first arm and the second arm have a plurality of field generator coils connected thereto.

13. The system of claim 12, wherein the first and second generator coils are configured to generate a magnetic field within a first control volume and a second control volume, respectively.

14. The system of claim 10, wherein the first arm is decoupled from the surgical bed platform so as to allow the bed to bend without placing direct pressure on the arm.

15. The system of claim 14, wherein the second arm is decoupled from the surgical bed platform as to allow the bed to bend without placing direct pressure on the arms.

16. The system of claim 10, wherein the first arm is hingedly attached to the brace and structurally supported by the brace.

17. A system, comprising:
a surgical bed platform including a first bed portion and a second bed portion, the second bed portion being movable relative to the first bed portion;
a brace disposed within the surgical bed platform and directly connected to the surgical bed platform;
a first hinged arm attached to the brace, including a first arm portion, a second arm portion, and a hinge connecting the first arm portion and the second arm portion, the first arm portion having a first field generator coil connected thereto, the second arm portion having a second field generator coil connected thereto, the first arm portion configured to rotate about the hinge relative to the second arm portion;
a second hinged arm attached to the brace, and positioned on opposing side of the surgical bed platform from the first arm, the second hinged arm having at least one field generator coil embedded therein, the second hinged arm positioned parallel to the first hinged arm; and
wherein the first hinged arm and the second hinged arm are independent from weight-bearing portions of the surgical bed platform.

18. The system of claim 17, further comprising a base connecting component is at a level of the surgical bed platform.

19. The system of claim 17, further comprising a base connecting component is below the surgical bed platform.

20. The system of claim 17, comprising a base supporting the surgical bed platform and a base connecting component that connects the first hinged arm to the second hinged arm.

* * * * *